United States Patent
Bruheim et al.

(10) Patent No.: US 10,525,068 B2
(45) Date of Patent: *Jan. 7, 2020

(54) ANTI-INFLAMMATORY PROPERTIES OF MARINE LIPID COMPOSITIONS

(71) Applicant: AKER BIOMARINE ANTARCTIC AS, Stamsund (NO)

(72) Inventors: Inge Bruheim, Volda (NO); Mikko Griinari, Espoo (FI); Sebastiano Banni, Cagliari (IT); Per Christian Saebo, Volda (NO); Erik Fuglseth, Molde (NO)

(73) Assignee: Aker BioMarine Antarctic AS, Stamsund (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/180,564

(22) Filed: Nov. 5, 2018

(65) Prior Publication Data

US 2019/0070203 A1    Mar. 7, 2019

Related U.S. Application Data

(63) Continuation of application No. 12/849,950, filed on Aug. 4, 2010, now Pat. No. 10,117,882, which is a continuation of application No. 11/800,229, filed on May 4, 2007, now abandoned.

(60) Provisional application No. 60/872,096, filed on Dec. 1, 2006, provisional application No. 60/798,027, filed on May 5, 2006, provisional application No. 60/798,030, filed on May 5, 2006, provisional application No. 60/798,026, filed on May 5, 2006.

(51) Int. Cl.
*A61K 31/685* (2006.01)
*C07F 9/10* (2006.01)

(52) U.S. Cl.
CPC .............. *A61K 31/685* (2013.01); *C07F 9/10* (2013.01)

(58) Field of Classification Search
None
See application file for complete search history.

(56) References Cited

U.S. PATENT DOCUMENTS

| 8,030,348 B2 | 10/2011 | Sampalis |
| 10,117,882 B2 * | 11/2018 | Bruheim |
| 2005/0130937 A1 | 6/2005 | Ben Dror et al. |

FOREIGN PATENT DOCUMENTS

| WO | 92/21335 | 12/1992 |
| WO | 97/26287 | 8/1996 |
| WO | 06/054183 | 5/2006 |

OTHER PUBLICATIONS

Stafford, R. and Dennis, E. "Lysophospholipids as Biosurfactants" Colloids and Surfaces, 30 (1988) 47-64.
"Silent Inflammation", The Cory Holly Institute, 2005, downloaded from http://www.coryholly.com/articles/article.cfm?d=89: on Feb. 20, 2008, pp. 1-2 of 2.
Autism-PDD.NET, "What is Autism?", 2003-2005, downloaded from www.autism-pdd.net/what-is-autism.html on Nov. 13, 2008, pp. 1-3 of 3.
Hosokawa M et. Al, "Preparation of Therapeutic Phospholipids through Procine Pancreatic Phopholipase A2-Mediated Esterification and Lipozyme-Mediated Acidolysis" Journal of the American Oil Chemists' Society, Springer, Berlin, De, vol. 72, No. 11, 1995, pp. 1287-1291.
Smith, L., "Acute Inflammation: the underlying mechanism in delayed onset muscle soreness?", 1991, Medicine & Science in Sports & Exercise, vol. 23 (5), pp. 542-551, only Abstract provided.
Morrison, W.R. "Lipids in cereal starches: A review" Journal of Cereal Science, 1988, vol. 8(1), pp. 1-15; abstract.

* cited by examiner

*Primary Examiner* — Savitha M Rao
*Assistant Examiner* — Gregg Polansky
(74) *Attorney, Agent, or Firm* — Casimir Jones S.C.; J. Mitchell Jones

(57) ABSTRACT

Novel marine lipid compositions comprising triglycerides and omega-3 rich phospholipids are described. The compositions are characterized by providing highly bioavailable omega-3, increased tissue incorporation of omega-3 and reduced concentration of pro-inflammatory cytokines.

14 Claims, 6 Drawing Sheets

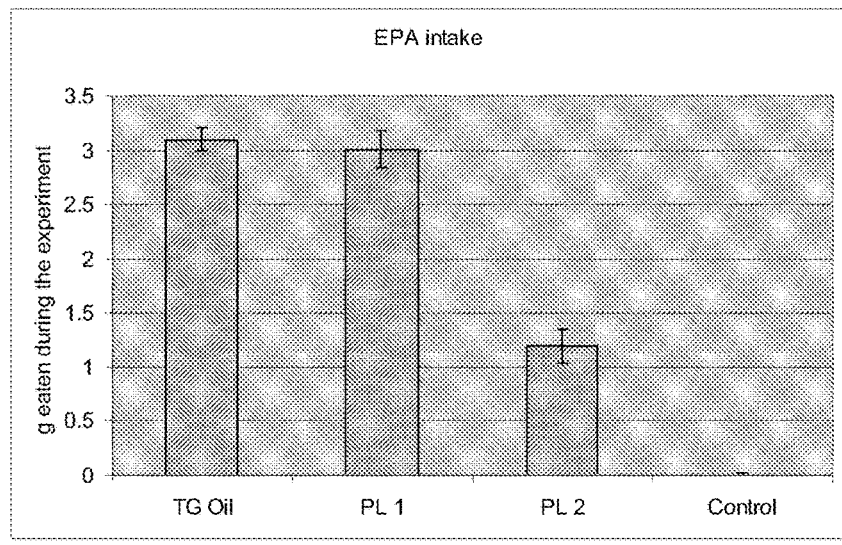
Figure 1. The total amount of EPA consumed during the four-week rat trial (mean ± SE).
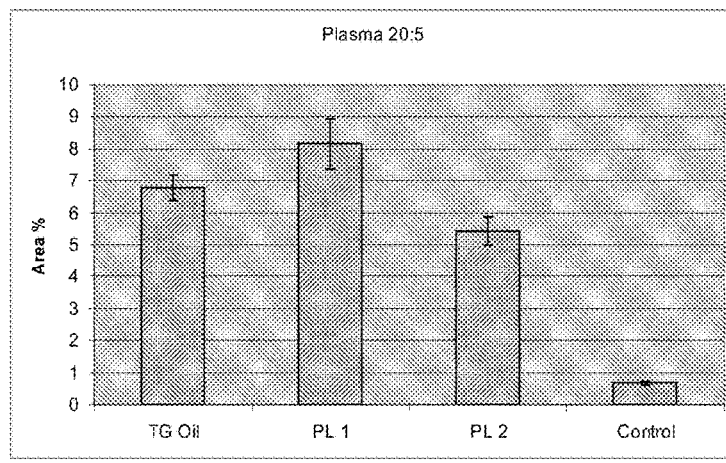
Figure 2. Relative EPA (20:5) content of plasma (mean ± SE; n = 6).

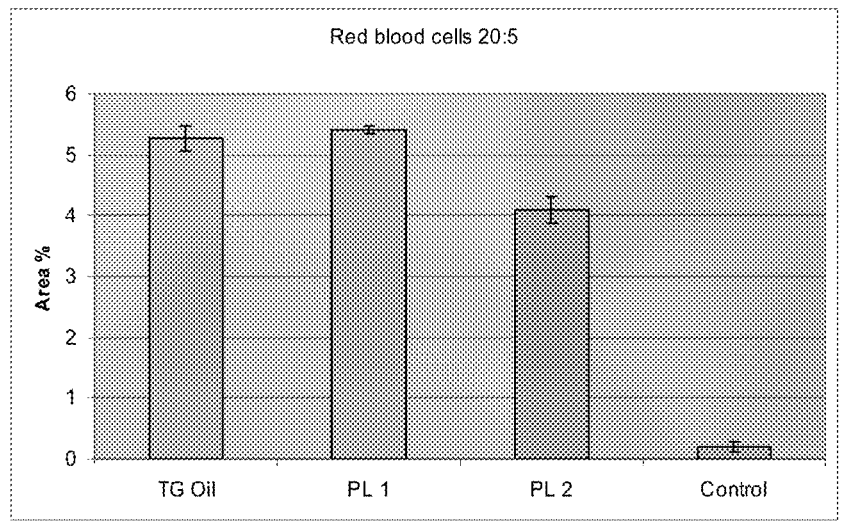
Figure 3. Relative 20:5 content of red blood cells (mean ± SE; n = 5-6).
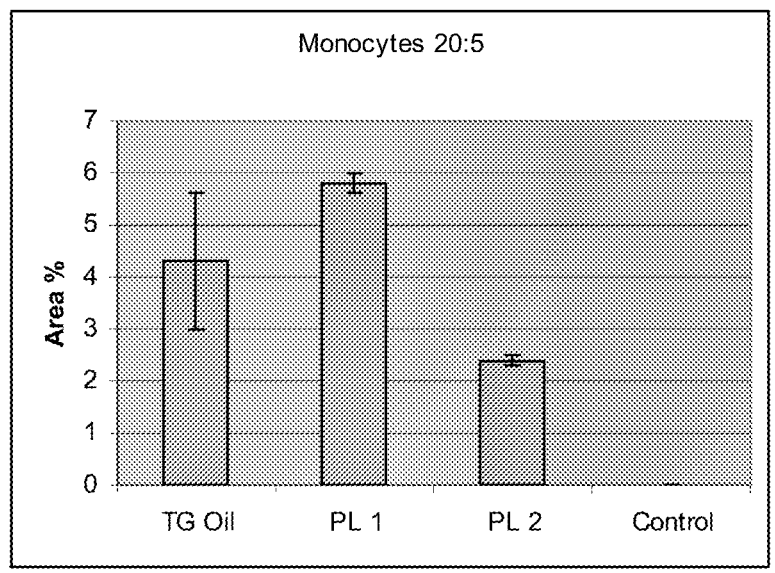
Figure 4. Relative 20:5 content of monocytes (mean ± SE; n = 5-6).

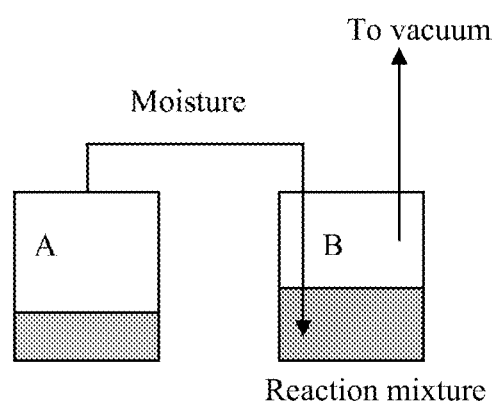
Figure 5. Schematic drawing of the experimental setup

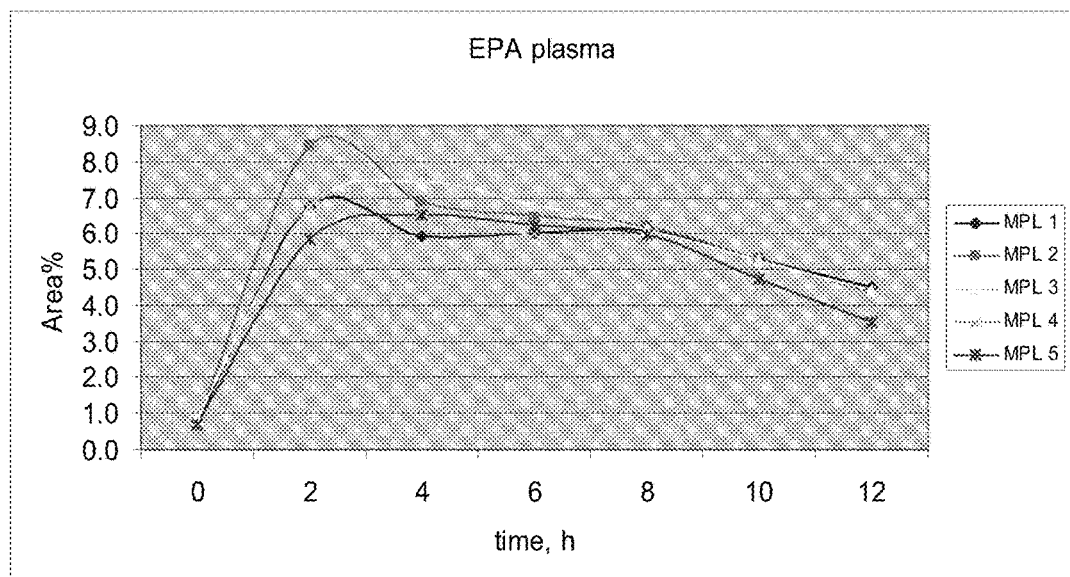
Figure 6. EPA levels in plasma as a function of hours after one bolus intake of a marine phospholipid composition.

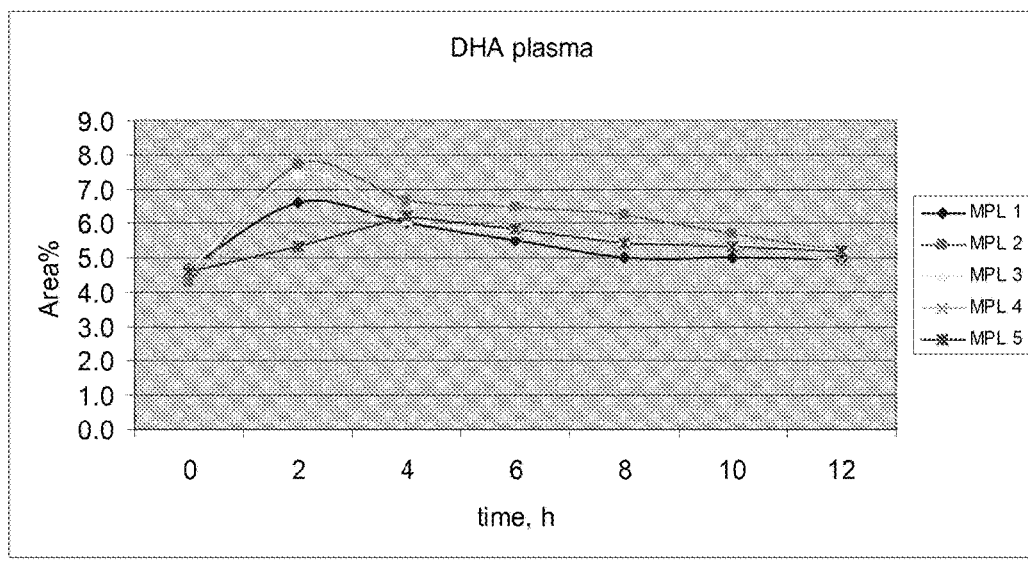
Figure 7. DHA levels in plasma as a function of hours after one bolus intake of a marine phospholipid composition

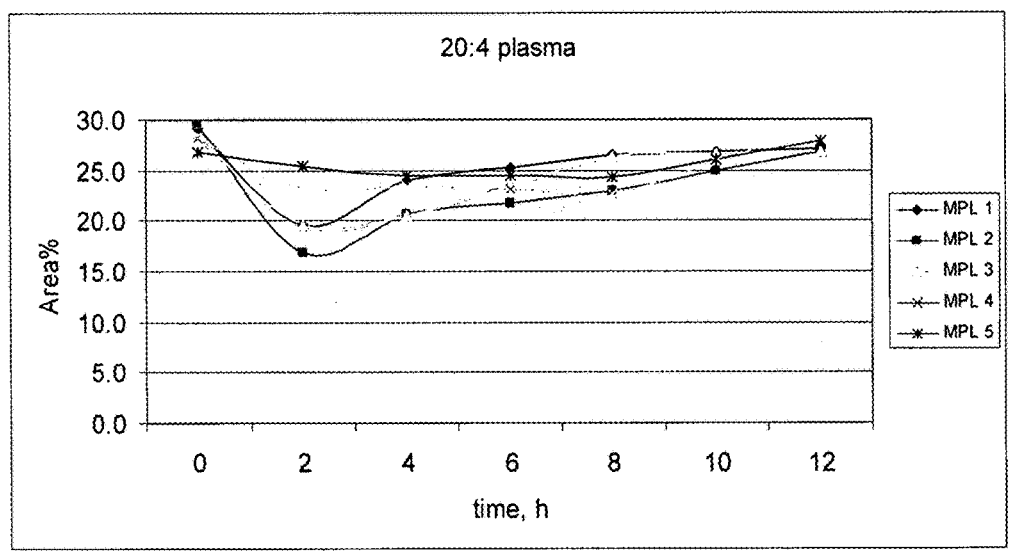
Figure 8. ARA levels in plasma as a function of hours after one bolus intake of a marine phospholipid composition

ANTI-INFLAMMATORY PROPERTIES OF MARINE LIPID COMPOSITIONS

CROSS REFERENCE TO RELATED APPLICATIONS

This application is a continuation of U.S. patent application Ser. No. 12/849,950, filed Aug. 4, 2010, now U.S. Pat. No. 10,117,882, which is a continuation of U.S. patent application Ser. No. 11/800,229, filed: May 4, 2007, which claims the benefit of U.S. Provisional Patent Applications Ser. Nos. 60/798,026, 60/798,027, and 60/798,030, all filed: May 5, 2006, and U.S. Provisional Patent Application Ser. No. 60/872,096, filed: Dec. 1, 2006, each of which is incorporated herein in their entireties.

FIELD OF THE INVENTION

The present invention relates to novel marine lipid compositions comprising combinations of omega-3 fatty acid rich functional phospholipids and omega-3 fatty acid rich triglycerides. In addition, food supplements, functional food, drugs and feed products comprising such compositions are provided along with methods of their use.

BACKGROUND OF THE INVENTION

Marine lipids such as omega-3 rich triglycerides and omega-3 rich phospholipids can be isolated from a number of different natural sources such as fish, crustaceans, plankton, seals, whales as well as algae using extraction technologies. In addition, they can be prepared industrially using chemical or bio-catalytical methods such as enzyme catalyzed transesterification of crude soy lecithin with fish oil fatty acids [1].

The anti-inflammatory properties of omega-3 fatty acids are well known and the use as an anti-inflammatory agent has been described both for triglycerides and phospholipids [2-3]. Actually, omega-3 fatty acids are famous for their anti-inflammatory properties, and it has been shown that omega-3 fatty acids alleviate the symptoms of a series of autoimmune, atherosclerotic and inflammatory diseases including inflammatory bowel diseases and rheumatoid arthritis [4-6]. Suppression of inflammation has been proposed as one of the strategies to slow down the progress of these diseases. Hence, this invention discloses the effect on marine lipid compositions on the concentration of markers of inflammation such as TNF-α and other cytokines such as interleukin-1β and interleukin 6. In addition, since arachidonic acid (AA) is the predominant precursor of the eicosanoid mediators of inflammatory responses (prostaglandins, thromboxanes and leukotrienes), this invention discloses the reduction of AA level and the improvement in the EPA/AA ratio in different lipid pools in tissues such as in the phospholipids isolated from adipose tissue, heart, testicles, plasma, brain and liver.

The bioavailability of EPA and DHA from fish oil triglycerides have been reported to be high in healthy adults. However, for certain conditions i.e. pathological conditions such as extrahepatic cholestasis and for pre-term infants the absorption can be low. For example it was shown that the absorption of DHA from egg lecithin in pre-term infants was 90% compared to 80% from triglycerides [7]. Absorption of long chain PUFA (AA and DHA) is less (75% and 62%, respectively) than the absorption of C18 PUFA (94%) in pre-term infants [8]. The difference between C18 PUFA and long chain PUFA absorption is likely to become less apparent in older children and adults. Sala-Vila et al [9-10] investigated the bioavailabilies of DHA-PL and DHA-TG in full term infants and found no differences based on plasma lipid enrichments. Valenzuela et al. [11] supplemented female rats with different forms of DHA including egg yolk PL and single cell algae TG. They found also no difference in absorption of DHA from PL and TG based on plasma lipid enrichments. However, the tissue and milk fat levels were higher in PL-DHA compared to the TG-DHA supplemented rats. These data indicate that although there were no differences in the bioavailability, efficacy with respect to tissue enrichment was higher for PL-DHA compared to TG-DHA. Furthermore, the relative absorption of EPA and DHA ethyl esters (4 g/d) compared to oleic acid calculated from peak concentrations was 94 and 100%, respectively. Estimates of relative absorption based on the area under the concentration curve indicated a relative absorption of 91% for EPA and 93% for DHA [12]. Bioavailability of C18:1, C18:2 and C18:3 in adult humans are close to 100% (note 94% in preterm infants). Thus the bioavailability of EPA and DHA delivered in different forms is, according to previous, work likely to be over 90%.

SUMMARY OF THE INVENTION

In some embodiments, the invention provides a composition comprising a triglyceride and a phospholipids in a ratio ranging from 1:10 to 10:1; said phospholipids having the following structure:

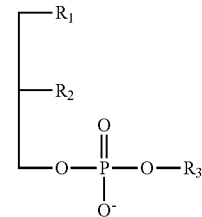

wherein R1 is OH or a fatty acid, R2 is OH or a fatty acid, and R3 is a mixture of H, choline, ethanolamine, inositol and serine, said phospholipid having at least 1% of DHA/EPA, said phospholipids have a concentration of OH in the range of 25-50%. In further embodiments, the invention provides a marine lipid composition characterized by providing higher uptake of omega-3 fatty acids into plasma as compared to administration of purified triglycerides, phospholipids, or natural marine phospholipids. In further embodiments, the invention provides a composition characterized by efficiently improving the AA/EPA ratio in plasma phospholipids as compared to administration of purified triglycerides, phospholipids, or natural marine phospholipids. In still other embodiments, the invention is a marine lipid composition characterized by efficiently increasing the concentration of omega-3 fatty acids in tissues as compared to administration of purified triglycerides, phospholipids, or natural marine phospholipids. In still further embodiments, the invention the composition is characterized by reducing the concentration of biomarkers of inflammation as compared to administration of purified triglycerides, phospholipids, or natural marine phospholipids. In other embodiments of the invention, the marine lipid composition is formulated into an animal feed, a food product, a food supplement and a drug.

In some embodiments, the present invention provides a composition comprising phospholipids having the following structure:

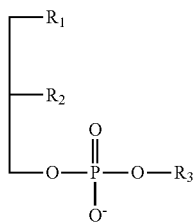

wherein R1 is OH or a fatty acid, R2 is OH or a fatty acid, and R3 is a mixture of H, choline, ethanolamine, inositol and serine, said phospholipid having at least 1% of DHA/EPA at positions R1 and/or R2 and from about 20-50% of OH at positions R1 and/or R2. In some embodiments, the composition is acylated in a range from about 55% to about 85%. In some embodiments, the omega-3 fatty acids are selected from the group consisting of EPA, DHA, DPA and α-linolenic acid (ALA). In some embodiments, the composition is substantially free of organic solvents and volatile organic compounds such as short chain fatty acids, short chain aldehydes and short chain ketones. In some embodiments, the composition has at least 5% of a combination of EPA and DHA esterified. In some embodiments, the composition has at least 10% of a combination of EPA and DHA esterified. In some embodiments, the composition has at least 20% of a combination of EPA and DHA esterified. In some embodiments, the composition has at least 30% of a combination of EPA and DHA esterified. In yet other embodiments, said composition contains from about 5%, 10%, 20% and 30% EPA/DHA attached to position 1 and/or position 2. In some embodiments, the composition has a ratio of EPA/DHA ranging from 1:1 to 4:1. In some embodiments, the composition has a ratio of EPA/DHA ranging from 2:1 to 4:1. In some embodiments, the composition is acylated in a range from 60% to 80%. In some embodiments, the composition is acylated in a range from 50% to 75%.

In some embodiments, the composition further comprises a lipid carrier in a ratio of from 1:10 to 10:1 to said phospholipids. In some embodiments, the lipid carrier and said phospholipids are in a ratio of from about 5:1 to 1:5. In some embodiments, the composition comprises from about 20% to about 90% of said phospholipid composition and from about 10% to about 50% of said lipid carrier. The present invention is not limited to any particular lipid carrier. In some embodiments, the lipid carrier is selected from the group consisting of a triglyceride, a diglyceride, an ethyl ester, and a methyl ester and combinations thereof. In some embodiments, the composition provides higher uptake of omega-3 fatty acids into plasma as compared to natural marine phospholipids when administered to subjects. In some embodiments, the composition improves the AA/EPA ratio in plasma phospholipids when administered to subjects as compared to natural marine phospholipids. In some embodiments, the composition increases the concentration of omega-3 fatty acids in tissues when administered to subjects as compared to natural marine phospholipids. In some embodiments, the composition reduces the concentration of biomarkers of inflammation when administered to subjects as compared to natural marine phospholipids. In some embodiments, the present invention provides a food product comprising the foregoing compositions. In some embodiments, the present invention provides an animal feed comprising the foregoing compositions. In some embodiments, the present invention provides a food supplement comprising the foregoing compositions. In some embodiments, the present invention provides a pharmaceutical composition comprising the foregoing compositions.

In some embodiments, the present invention provides methods of preparing a bioavailable omega-3 fatty acid composition comprising: a) providing a purified phospholipid composition comprising omega-3 fatty acid residues and a purified triglyceride composition comprising omega-3 fatty acid residues; b) combining said phospholipid composition and said triglyceride composition to form a bioavailable omega-3 fatty acid composition. In some embodiments, the bioavailable phospholipid composition is one of the compositions described above. In some embodiments, the methods further comprise the step of encapsulating said bioavailable omega-3 fatty acid composition. In some embodiments, the bioavailable omega-3 fatty acid composition has increased bioavailability as compared to purified triglycerides or phospholipids comprising omega-3 fatty acid residues. In some embodiments, the methods further comprise the step of packaging the bioavailable omega-3 fatty acid composition for use in functional foods. In some embodiments, the methods further comprise the step of assaying the bioavailable omega-3 fatty acid composition for bioavailability. In some embodiments, the methods further comprise administering the bioavailable omega-3 fatty acid composition to a patient. In some embodiments, the present invention provides a food product, animal feed, food supplement or pharmaceutical composition made by the foregoing process.

In some embodiments, the present invention provides methods for reducing symptoms of cognitive dysfunction in a child comprising administering an effective amount of a marine phospholipid composition, wherein said symptoms are selected from the group consisting of ability to complete task, ability to stay on task, ability to follow instructions, ability to complete assignments, psychomotor function, long term memory, short term memory, ability to make a decision, ability to follow through on decision, ability to self-sustain attention, ability to engage in conversations, sensitivity to surroundings, ability to plan, ability to carry out plan, ability to listen, interruptions in social situations, temper tantrums, level/frequency of frustration, level/frequency restlessness, frequency/level fidgeting, ability to exhibit delayed gratification, aggressiveness, demanding behavior/frequency of demanding behavior, sleep patterns, restive sleep, interrupted sleep, awakening behavior, disruptive behavior, ability to exhibit control in social situations, ability to extrapolate information and ability to integrate information. In some embodiments, the child exhibits one or more symptoms of Attention Deficit Hyperactivity Disorder (ADHD), is suspected of having ADHD, or has been diagnosed with ADHD. In some embodiments, the child exhibits one or more symptoms of autistic spectrum disorder, is suspected of having autistic spectrum disorder, or has been diagnosed with autistic spectrum disorder. In further embodiments, the present invention provides methods of increasing cognitive performance in an aging mammal comprising administering an effective amount of a marine phospholipid composition. In some embodiments, the cognitive performance is selected from the group consisting of memory loss, forgetfulness, short-term memory loss, aphasia, disorientation, disinhibition, and behavioral changes. In some embodiments, the mammal is a human. In some embodiments, the mammal is a pet selected from the group consisting of cats and dogs. In some embodiments, the mammal has symptoms of age-associated memory impairment or decline.

The foregoing methods are not limited to the use of any particular marine phospholipid composition. In some embodiments, the marine phospholipid composition comprises phospholipids having the following structure:

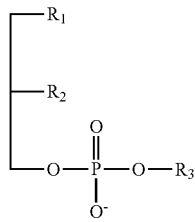

wherein R1 is OH or a fatty acid, R2 is OH or a fatty acid, and R3 is a mixture of H, choline, ethanolamine, inositol and serine, said phospholipid having at least 1% of omega-3 fatty acid moieties at positions R1 and/or R2. In some embodiments, the phospholipid composition comprises from about 20-50% of OH at positions R1 and/or R2. In some embodiments, the phospholipid composition further comprises a lipid carrier. In some embodiments, the phospholipid composition is prepared from natural marine phospholipids isolated from a marine organism. In some embodiments, the phospholipid composition is enzymatically prepared by reacting lecithin with DHA and EPA in the presence of an enzyme. In some embodiments, the lecithin is soybean or egg lecithin. In some embodiments, the omega-3 fatty acid moieties are selected from the group of EPA and DHA and combination thereof. In some embodiments, the effective amount of said phospholipid composition comprises from about 300 to about 1000 mg omega-3 fatty acids. In some embodiments, the phospholipid composition is administered orally. In some embodiments, the phospholipid composition is provided in a gel capsule or pill.

In some embodiments, the present invention provides methods of treating a subject by administration of a marine phospholipid composition comprising administering a marine phospholipid composition to said subject under conditions such that a desired condition is improved, wherein said conditions is selected from the group consisting of fertility, physical endurance, sports performance, muscle soreness, inflammation, auto-immune stimulation, metabolic syndrome, obesity and type II diabetes. In some embodiments, the subject is a human. In some embodiments, the subject is a companion animal. The present invention is not limited to any particular marine phospholipid composition. In some embodiments, the marine phospholipid composition comprises phospholipids having the following structure:

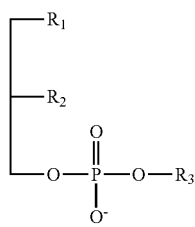

wherein R1 is OH or a fatty acid, R2 is OH or a fatty acid, and R3 is a mixture of H, choline, ethanolamine, inositol and serine, said phospholipid having at least 1% of omega-3 fatty acid moieties at positions R1 and/or R2. In some embodiments, the phospholipid composition comprises from about 20-50% of OH at positions R1 and/or R2. In some embodiments, the phospholipid composition is prepared from natural marine phospholipids isolated from a marine organism. In some embodiments, the composition further comprises a lipid carrier. In some embodiments, the phospholipid composition is enzymatically prepared by reacting lecithin with DHA and EPA in the presence of an enzyme. In some embodiments, the lecithin is soybean or egg lecithin. In some embodiments, the omega-3 fatty acid moieties are selected from the group of EPA and DHA and combination thereof. In some embodiments, the effective amount of said phospholipid composition comprises from about 300 to about 1000 mg omega-3 fatty acids. In some embodiments, the phospholipid composition is administered orally. In some embodiments, the phospholipid composition is provided in a gel capsule or pill. In some embodiments, the human is a male.

In some embodiments, the present invention provides methods for prophylactically treating a subject by administration of a marine phospholipid composition comprising administering a marine phospholipid composition to a subject under conditions such that an undesirable condition is prevented, wherein said undesirable condition is selected from the group consisting of weight gain, infertility, obesity, metabolic syndrome, diabetes type II, mortality in subjects with a high risk of sudden cardiac death, and induction of sustained ventricular tachycardia. In some embodiments, the subject is at risk for developing a condition selected from the group consisting of weight gain, obesity, metabolic syndrome, diabetes type II, mortality in subjects with a high risk of sudden cardiac death, and induction of sustained ventricular tachycardia.

In some embodiments, the subject is a human. In some embodiments, the subject is a companion animal. The present invention is not limited to any particular marine phospholipid composition. In some embodiments, the marine phospholipid composition comprises phospholipids having the following structure:

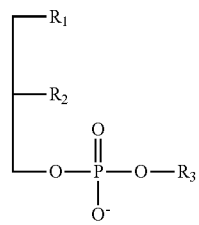

wherein R1 is OH or a fatty acid, R2 is OH or a fatty acid, and R3 is a mixture of H, choline, ethanolamine, inositol and serine, said phospholipid having at least 1% of omega-3 fatty acid moieties at positions R1 and/or R2. In some embodiments, the phospholipid composition comprises from about 20-50% of OH at positions R1 and/or R2. In some embodiments, the phospholipid composition is prepared from natural marine phospholipids isolated from a marine organism. In some embodiments, the composition further comprises a lipid carrier. In some embodiments, the phospholipid composition is enzymatically prepared by reacting lecithin with DHA and EPA in the presence of an enzyme. In some embodiments, the lecithin is soybean or egg lecithin. In some embodiments, the omega-3 fatty acid moieties are selected from the group of EPA and DHA and combination thereof. In some embodiments, the effective amount of said phospholipid composition comprises from about 300 to about 1000 mg omega-3 fatty acids. In some embodiments, the phospholipid composition is administered orally. In some embodiments, the phospholipid composition is provided in a gel capsule or pill.

DESCRIPTION OF THE FIGURES

FIG. 1. The total amount of EPA consumed during the four-week rat trial (mean±SE).

FIG. 2. Relative EPA (20:5) content of plasma (mean±SE; n=6).

FIG. 3. Relative 20:5 content of red blood cells (mean±SE; n=5-6).

FIG. 4. Relative 20:5 content of monocytes (mean±SE; n=5-6).

FIG. 5. Schematic drawing of experimental set-up.

FIG. 6. EPA levels in plasma as a function of hours after one bolus intake of a marine phospholipid composition.

FIG. 7. DHA levels in plasma as a function of hours after one bolus intake of a marine phospholipid composition.

FIG. 8. ARA levels in plasma as a function of hours after one bolus intake of a marine phospholipid composition.

DEFINITIONS

As used herein, "phospholipid" refers to an organic compound having the following general structure:

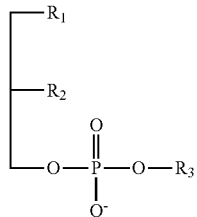

wherein R1 is a fatty acid residue or —OH, R2 is a fatty acid residue or —OH, and R3 is a —H or a nitrogen containing compound such as choline ($HOCH_2CH_2N^+(CH_3)_3OH^-$), ethanolamine ($HOCH_2CH_2NH_2$), inositol or serine. R1 and R2 cannot simultaneously be OH. When R3 is an —OH, the compound is a diacylglycerophosphate, while when R3 is a nitrogen-containing compound, the compound is a phosphatide such as lecithin, cephalin, phosphatidyl serine or plasmalogen.

The R1 site is herein referred to as position 1 of the phospholipid, the R2 site is herein referred to as position 2 of the phospholipid, and the R3 site is herein referred to as position 3 of the phospholipid.

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, 5,8,11, 14,17-eicosapentaenoic acid (EPA), 4,7,10,13,16,19-docosahexanoic acid (DHA) and 7,10,13,16,19-docosapentanoic acid (DPA).

As used herein, the term "bioavailability" refers to the degree and rate at which a substance (as a drug) is absorbed into a living system or is made available at the site of physiological activity.

As used herein, the term "functional food" refers to a food product to which a biologically active supplement has been added.

As used herein, the term "fish oil" refers to any oil obtained from a marine source e.g. tuna oil, seal oil and algae oil.

As used herein, the term "lipase" refers to any enzyme capable of hydrolyzing fatty acid esters As used herein, the term "food supplement" refers to a food product formulated as a dietary or nutritional supplement to be used as part of a diet.

As used herein, the term "acylation" means fatty acids attached to the phospholipid. 100% acylation means that there are no lyso- or glycerol-phospholipids.

DETAILED DESCRIPTION OF THE INVENTION

This invention discloses that the uptake/absorption of omega-3 fatty acids attached to phospholipids are dependent on the level of LPL and GPL. Preferably, in order to ensure maximum uptake the level of LPL should be in the range of 15-45% and the level of GPL should be 0%. Furthermore, this invention discloses that the pure PC transesterified with EPA/DHA have a different effect on gene expression in the liver than 40% PC transesterified with EPA/DHA. It is disclosed that the two compositions regulated around 40 genes differently. Furthermore, the invention discloses that the EPA/DHA ratio is important. The treatment containing a EPA/DHA ratio of 2:1 regulated key enzymes involved in the inflammatory response (NF-κB) in a positive way, the treatment containing a EPA/DHA ratio of 1:1 did not.

The present invention describes novel marine lipid compositions comprising an omega-3 containing phospholipid and a triacylglyceride (TG) in a ratio from about 1:10 to 10:1. Preferably the ratio is in the range of from about 3:1 to 1:3, more preferably the ratio is in the range of about 1:2 to 2:1. Preferably, the TG is a fish oil such as tuna oil, herring oil, menhaden oil, cod liver oil and algae oil. However, this invention is not limited to omega-3 containing oils as other TG sources are contemplated such as vegetable oils. The phospholipids in the composition have the following structure:

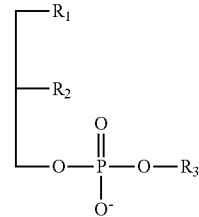

wherein R1 is OH or a fatty acid, R2 is OH or a fatty acid, and R3 is a mixture of H, choline, ethanolamine, inositol and serine. Attached to position 1 or position 2 are least 1% omega-3 fatty acids, preferably at least 5%, more preferably at least 10% omega-3 fatty acids, up to about 15%, 20%, 30%, 40%, 50%, or 60% omega-3 fatty acids. The omega-3 fatty acids can be EPA, DHA, DPA or C18:3 (n-3), most preferably the omega-3 fatty acids are EPA and DHA. The phospholipid composition preferably contains OH in position 1 or position 2 in a range of 25% to 50% in order to maximize absorption in-vivo.

In some embodiments, the present invention provides bioavailable and bioefficient omega-3 fatty acids. This invention shows that the novel marine lipid composition disclosed above enhances the uptake of the omega-3 fatty acid in vivo and incorporates omega-3 fatty acids more efficiently into tissues of adult rats than pure fish oil does. An embodiment of the invention is to use the marine lipid composition for efficient increase of omega-3 fatty acids in the liver, brain, adipose tissue, plasma, testicles and heart. Furthermore, this invention also discloses that the marine lipid compositions efficiently reduced the concentration of the pro-inflammatory precursor AA in total lipids and in phospholipids in tissues. It is disclosed that the concentration of AA in the different lipid pools in the liver, brain, adipose tissue, plasma, testicles and heart can be more efficiently reduced than using fish oil. Hence, the composition can be used to improve the EPA/AA ratio, which is a bio-marker of silent inflammation. The invention also discloses that the incorporation of the omega-3 fatty acids into monocytes is also more efficient using the claimed marine lipid composition as opposed to the fish oil. Yet another embodiment of the invention is to use the marine lipid composition to reduce chronic and acute inflammation in humans and in animals. Acute inflammation is mediated by granulocytes or polymorphonuclear leukocytes, while chronic inflammation is mediated by mononuclear cells such as monocytes. Monocytes protect against blood-borne pathogens and moves quickly to sites of infection in the tissues, secreting large amounts of pro-inflammatory prostaglandins. Furthermore, low grade chronic inflammation may be the underlying cause of many life-style related diseases such as obesity, arthritis, diabetes type II, metabolic syndrome, Alzheimer's disease, osteoarthritis, inflammatory bowel disease, allergy and asthma [14]. Hence, the marine lipid composition can be used to treat and prevent diseases linked to chronic inflammation. This invention discloses that the inflammatory response of monocytes harvested from animals in lower in animals treated with the marine lipid composition compared to fish oil. The concentrations of the pro-inflammatory cytokines such as interleukin-1β, interleukin-6 as well as tumor necrosis factor α (TNF-α) were reduced for the group fed the marine lipid composition compared to fish oil. These cytokines are important markers of real inflammation as for examples Il-1β induces fever. Il-6 also induces fever in addition to being linked to the acute phase response. TNF-α is involved in systemic inflammation as well and is released by white blood cells in the case of damage. It has a range of different biological effects such as increasing insulin resistance, stimulating the acute phase response in the liver and affecting the hypothalamus causing appetite suppression and fever.

This invention also discloses that the fatty acid composition of the brain and adipose tissue phospholipids changes after in take of omega-3 fatty acids for 30 days. A significant reduction of the arachidonic acids can be found in the phospholipids in the brain and adipose tissue for the rats given either the EPA- or DHA-rich PL diets (PL 1 and PL 2, respectively). This may affect the inflammatory response in this tissue and thereby have a great impact on cognitive diseases/conditions such as Parkinson's or and Alzheimer's where the inflammatory component is fundamental for the progression of the disease. This invention also discloses that the reduction of ARA is present also in the sn-2 position of the phospholipids in the brain. This is very important as the pro-inflammatory eicosanoids are produced from ARA, which are catalytically hydrolyzed from position 2 on the phospholipid by the action of phospholipase A2. The phospholipase A2 is released after stimuli at the cell wall, it then moves to the nuclear membrane where the hydrolysis of the phospholipid takes place.

In adipose tissue, accumulation of EPA and DHA in both total lipids (table 3) and PLs (table 8) is substantial when omega-3 supplements were fed and negligible when the control diet was fed. The increase was more pronounced in total lipids, which mainly consists of triglycerides (99% of fat cell lipid content). This invention demonstrates that omega-3 phospholipids can increase the accumulation of EPA/DHA into adipose tissue. This is important as the adipose tissue can function as a reservoir for these fatty acids. Arachidonic acid concentration in total lipids was higher in omega-3 supplemented animals, showing probably an increase of lipoprotein lipase activity, in agreement with the ability of omega 3 in decreasing plasma TAGs concentration. On the other hand, arachidonic acid levels in adipose tissue PLs were significantly lower in omega-3 supplemented animals than the levels in controls. Peculiar enough, the PL-EPA diet was the most efficient in decreasing arachidonic acid. In addition, the invention discloses that the reduction of ARA is also observed in the sn-2 position of the phospholipids of the omega-3 supplemented animals. This is very important as the pro-inflammatory eicosanoids are produced from ARA, which are catalytically hydrolyzed from position 2 on the phospholipid by the action of phospholipase A2. The phospholipase A2 is released after stimuli at the cell wall, it then moves to the nuclear membrane where the hydrolysis of the phospholipid takes place. The reduction of ARA in position 2 on the phospholipids may affect the inflammatory response in this tissue, which may have practical application in different pathologies of the adipose tissue and in its physiological activity of accumulation and release of fatty acids.

Fatty acid data from brain are well in line with the data from adipose tissue. Also in this tissue, we found a significant decrease of arachidonic acid in PLs, but surprisingly, only with PL-EPA and PL-DHA (table 7). On the other hand, DHA levels in both total lipids and PLs were not influenced by the omega-3 diets, while there was a small but significant increase in EPA levels. Lack of increase in DHA levels is likely to be attributable to the fact that the rats in this study were adults and pass the stage in development where they incorporate DHA in the brain (mainly PE). On the other hand, EPA being present at low concentration has more margin to increase. Furthermore, this may affect the inflammatory response in this tissue, which may have a great impact in such diseases as Parkinson's and Alzheimer's where the inflammatory component is fundamental for the progression of the disease. Positional distribution of arachidonic acid show that the ARA content is reduced for the EPA-PL groups, as stated before this is very important as it influences the pro-inflammatory eicosanoid production.

In liver, as expected, we found for all omega-3 groups a significant increase of EPA and DHA and decrease of arachidonic acid. No great differences were expected between total lipids and PLs because about 80% of liver total lipids are PLs (table 4, 9 and 14).

Heart total lipids and PLs (table 6 and table 11, respectively) showed a strong increase of EPA and DHA with a concomitant decrease of arachidonic acid when omega-3 supplements were fed. The strong decrease in the omega-6/omega-3 ratio in heart lipids is important considering the possible impact on the anti-inflammatory potential. Observed change in heart tissue fatty acids (increase of fatty acids with 6 or 5 double bonds) also suggests a possible increase in membrane fluidity. This change was most striking in the PL-DHA group where the increase of DHA was significantly higher than the increase in the TG-oil and PL-EPA groups. The fluidity of myocardium cell membrane seems to play an important role in controlling arrhythmia. Ventricular arrhythmia, is one of the main causes of sudden cardiac death. Furthermore, atrial fibrillation is another pathological state with a high incidence and important health consequences.

Testicular long chain PUFAs are of special interest because there is a high rate of production of prostaglandins from the omega-6 PUFA (arachidonic acid mainly) into the semen or seminal fluid. High rate of prostaglandin production does not indicate an active inflammatory process but a stimulus for the uterus smooth muscle to favour male fertility. An omega-3 induced decrease of arachidonic acid as observed in other tissue could be detrimental to the male fertility if it occurred also in testis. Furthermore, testicular tissue has also a high level of DPA (22:5 omega-6), which may serve as a reservoir for arachidonic acid. Arachidonic acid could be formed according to the need, through the retroconversion mechanism in the peroxisomes. A similar mechanism may take place with DHA to form EPA in other tissues. Our data (table 5) show an increase of EPA and DHA and a small decrease of arachidonic acid in the total lipids fraction when omega-3 fatty acids are fed. However, there is no change in arachidonic acid levels in PL when TG-oil and PL-EPA are fed and interestingly a significant increase in the PL-DHA group. Furthermore, DPA n-6 concentration in total lipids was not influenced by omega-3 supplementation but there was a significant increase in DPA in the PL-EPA group (table 5). Overall, these data seem to indicate that the diets with omega-3 did not change the arachidonic and DPA n-6 concentrations in a way that would predict negative effects on male fertility. In contrast, increase in arachidonic acid content of testicular PLs (table 10) when PL-DHA was fed and increase in DPA when PL-EPA was fed could be interpreted to be positively associated with male fertility.

Another embodiment of the invention is to formulate the marine lipid compositions into a feed product for the purpose of reducing low-grade chronic inflammation in animals. It can also be formulated into a food product and given to humans for the same purpose. Furthermore, it can be formulated as a functional food product, as a drug or as food supplement.

In some embodiments, the compositions of this invention are contained in acceptable excipients and/or carriers for oral consumption. The actual form of the carrier, and thus, the compositions itself, is not critical. The carrier may be a liquid, gel, gelcap, capsule, powder, solid tablet (coated or non-coated), tea, or the like. The composition is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

In other embodiments, the composition contains no traces of organic solvents which is an important property regarding the safety of consuming such compounds. Phospholipids prepared using chemical or enzymatic methods in the presence of organic solvents may contain residual solvents that may be a health hazard. VOC are often co-extracted when marine phospholipids are extracted, such VOC's may contribute to the smell taste of the phospholipids.

In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The compositions of the present invention may also be formulated with a number of other compounds. These compounds and substances add to the palatability or sensory perception of the particles (e.g., flavorings and colorings) or improve the nutritional value of the particles (e.g., minerals, vitamins, phytonutrients, antioxidants, etc.).

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In further embodiments, the compositions comprise at least one food flavoring such as acetaldehyde (ethanal), acetoin (acetyl methylcarbinol), anethole (parapropenyl anisole), benzaldehyde (benzoic aldehyde), N-butyric acid (butanoic acid), d- or l-carvone (carvol), cinnamaldehyde (cinnamic aldehyde), citral (2,6-dimethyloctadien-2,6-al-8, gera-nial, neral), decanal (N-decylaldehyde, capraldehyde, capric aldehyde, caprinaldehyde, aldehyde C-10), ethyl acetate, ethyl butyrate, 3-methyl-3-phenyl glycidic acid ethyl ester (ethyl-methyl-phenyl-glycidate, strawberry aldehyde, C-16 aldehyde), ethyl vanillin, geraniol (3,7-dimethyl-2,6 and 3,6-octadien-1-ol), geranyl acetate (geraniol acetate), limonene (d-, l-, and dl-), linalool (linalol, 3,7-dimethyl-1,6-octadien-3-ol), linalyl acetate (bergamol), methyl anthranilate (methyl-2-aminobenzoate), piperonal (3,4-methylenedioxy-benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia, (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum-graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papayer somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron, tumeric, tumeric and oleoresin).

In still further embodiments, the compositions comprise at least one phytonutrient (e.g., soy isoflavonoids, oligomeric proanthcyanidins, indol-3-carbinol, sulforaphone, fibrous ligands, plant phytosterols, ferulic acid, anthocyanocides, triterpenes, omega 3/6 fatty acids, conjugated fatty acids such as conjugated linoleic acid and conjugated linolenic acid, polyacetylene, quinones, terpenes, cathechins, gallates, and quercitin). Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, *ginkgo biloba*, primrose (evening primrose oil), red clover, burdock root, dandelion, parsley, rose hips, milk thistle, ginger, Siberian ginseng, rosemary, curcumin, garlic, lycopene, grapefruit seed extract, spinach, and broccoli.

In still other embodiments, the compositions comprise at least one vitamin (e.g., vitamin A, thiamin (B1), riboflavin (B2), pyridoxine (B6), cyanocobalamin (B12), biotin, ascorbic acid (vitamin C), retinoic acid (vitamin D), vitamin E, folic acid and other folates, vitamin K, niacin, and pantothenic acid). In some embodiments, the particles comprise at least one mineral (e.g., sodium, potassium, magnesium, calcium, phosphorus, chlorine, iron, zinc, manganese, flourine, copper, molybdenum, chromium, selenium, and iodine). In some particularly preferred embodiments, a dosage of a plurality of particles includes vitamins or minerals in the range of the recommended daily allowance (RDA) as specified by the United States Department of Agriculture. In still other embodiments, the particles comprise an amino acid supplement formula in which at least one amino acid is included (e.g., 1-carnitine or tryptophan).

Transesterification of phosphatidylcholine (PC) under solvent free conditions has been performed by Haraldsson et al in 1999 [15], with the results of high incorporation of EPA/DHA and with the following hydrolysis profile PC/LPC/GPC=39/44/17. Extensive hydrolysis and by-product formation is generally considered a problem with transesterification reactions, resulting in low product yields. This invention discloses a process for transesterification of crude soybean lecithin (mixture of PC, PE and PI). In the first step, the lecithin is hydrolyzed using a lipase in the presence of water (pH=8). The use of a variety of lipases is contemplated, including, but not limited to, *Thermomyces Lanuginosus* lipase, *Rhizomucor miehei* lipase, *Candida Antarctica* lipase, *Pseudomonas fluorescence* lipase, and *Mucor javanicus* lipase. The first step takes around 24 hours and results in a product comprising predominantly of lyso-phospholipids and glycerophospholipids such as PC/LPC/GPC=0/15/85. In the second step, free fatty acids are added such as EPA and DHA, however any omega-3 fatty acid is contemplated. Next a strong vacuum is applied to the reaction vessel for 72 hours. However, the reaction length can be varied in order to obtain a composition with the desired amount of phospholipids and lyso-phospholipids. By extending the reaction time beyond 72 hours, a product comprising more than 65% phospholipids can be obtained. Next, a lipid carrier is added to the reaction mixture in order to reduce the viscosity of the solution. The added amount of triglycerides can be 10%, 20%, 30%, 40% or more, it depends on the requested viscosity of the final product. The lipid carrier can be a fish oil such as tuna oil, menhaden oil and herring oil, or any triglyceride, diglyceride, ethyl- or methylester of a fatty acid. In the final step, the product is subjected to a molecular distillation and the free fatty acids are removed, resulting in a final product comprising of phospholipids (lyso-phospholipids and phospholipids) and triglycerides in a ratio of preferably 2:1.

This invention further discloses a process for the enzymatic transesterification/esterification of phospholipids with fatty acids alkyl esters or free fatty acids in an evacuated vessel (B). A reduced pressure is applied to the vessel B (0.001-30 mbar) and water vapor (moisture) is allowed to enter the reaction mixture through a tube from a second vessel (A) (FIG. 5 for schematic drawing of the experimental setup). The water in vessel A is heated to 25-30° C. By adding moisture to an evacuated reaction vessel the rate of reaction could either be increased of the lipase dosage could be reduced. In addition, the reuse of the enzymes was improved. Finally, a novel marine phospholipid composition was prepared characterized by being acylated in the range of 55%-85%, having at least 5% EPA and/or DHA esterified, having a EPA/DHA ratio of at least 1.

Accordingly, in preferred embodiments, the present invention utilizes a phospholipid, preferably a phosphatide such as lecithin. The present invention is not limited to the use of any particular phospholipid. Indeed, the use of a variety of phospholipids is contemplated. In some embodiments, the phospholipid is a phosphatidic or lysophosphatidic acid. In more preferred embodiments, the phospholipid is a mixture of phosphatides such as phosphatidylcholine, phosphatidylethnolamine, phosphatidylserine and phosphatidylinositol. The present invention is not limited to the use of any particular source of phospholipids. In some embodiments, the phospholipids are from soybeans, while in other embodiments, the phospholipids are from eggs. In particularly preferred embodiments, the phospholipids utilized are commercially available, such as Alcolec 40P® from American Lecithin Company Inc (Oxford, Conn., USA). The present invention is not limited to the use of any particular enzyme. Indeed, the use of a variety of enzymes is contemplated, including, but not limited to *Thermomyces Lanuginosus* lipase, *Rhizomucor miehei* lipase, *Candida Antarctica* lipase, *Pseudomonas fluorescence* lipase, and *Mucor javanicus* lipase. This invention is not limited to any particular fatty acid alkyl ester either. This includes, but not limited to: decanoic acid (10:0), undecanoic acid (11:0), 10-undecanoic acid (11:1), lauric acid (12:0), cis-5-dodecanoic acid (12:1), tridecanoic acid (13:0), myristic acid (14:0), myristoleic acid (cis-9-tetradecenoic acid, 14:1), pentadecanoic acid (15:0), palmitic acid (16:0), palmitoleic acid (cis-9-hexadecenoic acid, 16:1), heptadecanoic acid (17:1), stearic acid (18:0), elaidic acid (trans-9-octadecenoic acid, 18:1), oleic acid (cis-9-octadecenoic acid, 18:1), nonadecanoic acid (19:0), eicosanoic acid (20:0), cis-11-eicosenoic acid (20:1), 11,14-eicosadienoic acid (20:2), heneicosanoic acid (21:0), docosanoic acid (22:0), erucic acid (cis-13-docosenoic acid, 22:1), tricosanoic acid (23:0), tetracosanoic acid (24:0), nervonic acid (24:1), pentacosanoic acid (25:0), hexacosanoic acid (26:0), heptacosanoic acid (27:0), octacosanoic acid (28:0), nonacosanoic acid (29:0), triacosanoic acid (30:0), vaccenic acid (t-11-octadecenoic acid, 18:1), tariric acid (octadec-6-ynoic acid, 18:1), and ricinoleic acid (12-hydroxyoctadec-cis-9-enoic acid, 18:1) and ω3, ω6, and ω9 fatty acyl residues such as 9,12,15-octadecatrienoic acid (α-linolenic acid) [18:3, ω3]; 6,9,12,15-octadecatetraenoic acid (stearidonic acid) [18:4, ω3]; 11,14,17-eicosatrienoic acid (dihomo-α-linolenic acid) [20:3, ω3]; 8,11,14,17-eicosatetraenoic acid [20:4, ω3], 5,8,11,14,17-eicosapentaenoic acid [20:5, ω3]; 7,10,13,16,19-docosapentaenoic acid [22:5, ω3]; 4,7,10,13,16,19-docosahexaenoic acid [22:6, ω3]; 9,12-octadecadienoic acid (linoleic acid) [18:2, ω6]; 6,9,12-octadecatrienoic acid (γ-linolenic acid) [18:3, ω6]; 8,11,14-eicosatrienoic acid (dihomo-γ-linolenic acid) [20:3 ω6]; 5,8,11,14-eicosatetraenoic acid (arachidonic acid) [20: 4, ω6]; 7,10,13,16-docosatetraenoic acid [22:4, ω6]; 4,7,10, 13,16-docosapentaenoic acid [22:5, ω6]; 6,9-octadecadienoic acid [18:2, ω9]; 8,11-eicosadienoic acid [20:2, ω9]; 5,8,11-eicosatrienoic acid (Mead acid) [20:3, ω9]; t10,c12 octadecadienoic acid; c10,t12 octadecadienoic acid; c9,t11 octadecadienoic acid; and t9,c11 octadecadienoic acid. Moreover, acyl residues may be conjugated, hydroxylated, epoxidated or hydroxyepoxidated acyl residues.

Marine phospholipids extracted from marine sources have a characteristic smell and taste of rancid fish. The GC profile of the volatiles confirms the presence of these degradation products, such as short chain aldehydes and carboxylic acids. In preferred embodiments, the synthetic marine phospholipid compositions of the present invention are substantially free of volatile organic compounds and are therefore much more suitable as a food supplement for humans and animals. Accordingly, in preferred compositions, the present invention provides synthetic marine phospholipids compositions having high or increased palatability, wherein the high or increased palatability is due to low levels of organic solvents and/or volatile organic compounds. In preferred embodiments, palatability is assayed by feeding the composition to a panel of subjects, preferably human. In more preferred embodiments, the phospholipids compositions have high or increased palatability as compared to naturally extracted marine phospholipids. In other preferred embodiments, the synthetic marine phospholipids compositions of the present invention are safe for oral administration.

EXPERIMENTAL

Example 1

The difference in bioavailability and bioefficacy between the marine lipid composition of the present invention and a fish oil were investigated in a rat experiment. The rat feed was prepared using AIN-93 except that soybean oil was removed from the feed. The pelleted AIN-93 diet was ground and the marine lipid compositions (PL 1 and PL 2) as well as fish oil (TG oil) and control were added to this ground feed. The marine lipid compositions were prepared using enzymatic (lipase) catalyzed transesterification of soy lecithin with fish oil fatty acids according to the method described in Example 4, followed by the addition of a triglyceride carrier and short path distillation. The concentration of EPA, DHA and 18:3 n-3 in the different diets can be seen in the table below (table 1).

TABLE 1

Amount of different fatty acid in the final feed products

| | | g/100 g EPA | g/100 g DHA | g/100 g 18:3n3 | SUM g/100 g EPA + DHA + 18:3n3 |
|---|---|---|---|---|---|
| Control | T4 | 0 | 0 | 0.26 | 0.26 |
| TG Oil | T1 | 0.61 | 0.39 | 0.24 | 1.23 |
| PL 1 | T2 | 0.61 | 0.35 | 0.26 | 1.22 |
| PL 2 | T3 | 0.24 | 0.73 | 0.26 | 1.23 |

Thirty six newly weaned male Sprague Dawley rats (start weight 168±11 g) were used in the experiment. The rats were initially given low-essential oil rat feed, containing 20 g of sunflower oil and 10 g of flaxseed oil per kg of feed, for one week. After the first week, modified AIN-93 diet powder without the test oil was given to rats ad libitum until the start of the experiment. Feeding of rats was stopped 12 hours before the sampling, 30 days after the start of feeding. Each rat was individually anaesthetized with carbon dioxide, weighed and euthanized with cervical dislocation. Next, blood was sampled and centrifuged to separate plasma and blood cells. Then abdominal skin was removed and 70 ml of sterile Hepes-Hanks was injected into the peritoneal cavity to collect intraperitoneal lymphocytes. The abdomen was gently massaged for about 3 minutes after which the buffer solution was drained and centrifuged in Falcon tubes (200× g, 10 min) to collect the cells. The cells were resuspended into 1 ml of freezing fluid (10% DMSO, 90% fetal bovine serum) in 1.5 ml Eppendorf tubes. These tubes were then frozen to dry ice temperature for one hour by immersing the tubes in isopropanol placed on dry ice. This enabled a slower freezing rate than by putting the cells directly on dry ice. In the laboratory, the cells were stored overnight at −80° C. and then stored in liquid nitrogen. The derivatization of the lipids in order to perform gas chromatographic (GC) analysis was carried accordingly to [16]. The run conditions for the GC were according to [17]. The growth of rats did not differ between the feeding groups (data not shown). The intake of feed, and the intake fatty acids thereof, was monitored by keeping the rats in metabolic cages which allows the measurement of eaten and uneaten portion of feed. The PL 1 test group consumed somewhat less EPA than the TG oil group, whereas the PL 2 and the control group consumed much less EPA than both the PL 1 and the TG oil groups (FIG. 1). The amount of EPA in plasma varied between the groups and the results are shown FIG. 2. Even though the estimated intake of EPA was higher in the TG Oil group than the PL 1 group, the area % of EPA measured in plasma for PL1 was higher than for TG oil. Indicating a higher bioavailability of EPA from of PL 1 than from the TG oil. Furthermore, this was also observed in the FA profile of the red blood cells and the monocytes (FIG. 3 and FIG. 4, respectively). Demonstrating that the PL 1 composition was more efficient in enriching these cells with omega-3 than the TG oil group, hence being more bioefficient than TG.

Example 2

The total fatty acid profile for the lipids in the brains (table 2), adipose tissue (table 3), liver (table 4), testicles (table 5) and heart (table 6) were isolated from the rats in example 1. The PL 1 composition increases the DHA content in brain and adipose tissue more than the TG composition. The PL 1 composition increase the EPA content in the adipose tissue more than the TG composition. It is to be observed that the PL1 composition increases the EPA/DHA content in the phospholipids and in the total lipids of the different tissues as well as reduces the AA/EPA ratio more than the TG oil composition.

TABLE 2

Fatty acid profile of the total lipids isolated from the rat brain (mmol/g lipids).

|  | 18:1 | 18:2 | 18:3 n3 | 20:3 | ARA | EPA | 22:4 | 22:5 n6 | 22:5 n3 | DHA |
|---|---|---|---|---|---|---|---|---|---|---|
| TG-oil | 370 | 12 | 0.35 | 5.7 | 153.7 | 2.2 | 68.5 | 5.6 | 5.0 | 191.4 |
| PL-1 | 399 | 12 | 0.33 | 7.2 | 160.7 | 2.2 | 70.2 | 7.2 | 5.7 | 203.3 |
| PL-2 | 345 | 13 | 0.33 | 5.7 | 141.6 | 1.7 | 60.8 | 5.8 | 3.4 | 190.3 |
| Control | 363 | 12 | 0.30 | 5.2 | 174.9 | 0.1 | 81.4 | 7.6 | 1.7 | 189.6 |

TABLE 3

Fatty acid profile of the total lipids isolated from adipose tissue (mmol/g lipids).

|  | 18:1 | 18:2 | 18:3 n3 | 20:3 | ARA | EPA | 22:4 | 22:5 n6 | 22:5 n3 | DHA |
|---|---|---|---|---|---|---|---|---|---|---|
| TG-oil | 350 | 306 | 40.2 | 1.4 | 6.3 | 21.7 | 6.3 | 0.9 | 11.3 | 27.5 |
| PL-1 | 500 | 236 | 58.2 | 1.9 | 7.0 | 24.0 | 7.0 | 1.0 | 7.2 | 30.1 |
| PL-2 | 420 | 536 | 45.7 | 2.4 | 6.8 | 12.8 | 6.8 | 2.7 | 104.0 | 50.9 |
| Control | 419 | 113 | 28.2 | 0.8 | 3.8 | 0.3 | 3.8 | 0.6 | 26.1 | 0.8 |

TABLE 4

Fatty acid profile of the total lipids in liver (mmol/g lipids).

|  | 18:1 | 18:2 | 18:3 n3 | 20:3 | ARA | EPA | 22:4 | 22:5 n6 | 22:5 n3 | DHA |
|---|---|---|---|---|---|---|---|---|---|---|
| TG-oil | 304.2 | 514.1 | 31.9 | 13.2 | 278.9 | 147.8 | 2.5 | 2.9 | 49.9 | 272.8 |
| PL-1 | 264.3 | 501.6 | 28.1 | 12.8 | 317.3 | 120.2 | 2.4 | 2.6 | 49.8 | 259.0 |
| PL-2 | 226.6 | 462.7 | 19.9 | 12.3 | 289.0 | 80.4 | 3.0 | 5.5 | 30.4 | 263.1 |
| Control | 359.2 | 493.7 | 21.7 | 8.9 | 480.9 | 9.2 | 12.0 | 4.5 | 14.7 | 145.8 |

TABLE 5

Fatty acid profile of the total lipids in testicles.

| nmoles FA/mg lipids | 18:4 | 20:5 n3 | 18:3 n6 | 18:3 | 22:6 | 16:1 | 20:4 | 18:2 | 22:5 | 20:3 | 20:3 n9 | 22:4 | 18:1 |
|---|---|---|---|---|---|---|---|---|---|---|---|---|---|
| TG-oil | 3.2 | 17.0 | 11.7 | 1.8 | 56.6 | 47.6 | 280.1 | 195.1 | 6.9 | 285.6 | 3.7 | 56.2 | 326.8 |
| PL-1 | 0.6 | 10.8 | 9.2 | 1.7 | 52.4 | 35.6 | 294.9 | 210.1 | 6.1 | 294.2 | 3.4 | 61.3 | 348.3 |
| PL-2 | 2.4 | 6.1 | 1.7 | 2.0 | 56.0 | 0.0 | 310.8 | 156.5 | 2.4 | 345.3 | 6.2 | 59.5 | 332.5 |
| Control | 1.8 | 1.1 | 1.6 | 2.0 | 27.2 | 0.0 | 335.5 | 162.2 | 1.3 | 319.1 | 5.8 | 78.7 | 330.1 |

TABLE 6

Fatty acid profile of the total lipids in heart.

| nmoles FA/mg lipids | 18:4 | 20:5 | n3 18:3 | n6 18:3 | 22:6 | 16:1 | 20:4 | 18:2 | 22:5 | 20:3 | 20:3 n9 | 22:4 | 18:1 |
|---|---|---|---|---|---|---|---|---|---|---|---|---|---|
| TG-oil | 2.0 | 44.7 | 20.2 | 0.9 | 314.0 | 49.7 | 279.6 | 787.9 | 4.0 | 6.8 | | 3.0 | 288.9 |
| PL-1 | 1.5 | 45.0 | 25.6 | 0.8 | 314.4 | 44.6 | 300.4 | 789.0 | 4.4 | 7.2 | | 3.3 | 276.6 |
| PL-2 | 0.2 | 29.1 | 9.9 | 0.4 | 372.1 | 30.1 | 291.0 | 690.3 | 9.0 | 6.3 | 1.5 | 4.4 | 237.0 |
| Control | 0.0 | 2.9 | 7.2 | 0.7 | 209.9 | | 495.8 | 756.2 | 14.7 | 6.2 | 2.4 | 30.3 | 289.5 |

Example 3

The fatty acid profile of the phospholipids isolated from the brain (table 7), adipose tissue (table 8), liver (table 9), testicles (table 10) and heart (Table 11) in the rats from example 1 were determined.

TABLE 7

Fatty acid profile of the phospholipids isolated from the brain (mmol/g lipids).

| | 18:1 | 18:2 | 18:3 n3 | 20:3 | ARA | EPA | 22:4 | 22:5 n6 | 22:5 n3 | DHA |
|---|---|---|---|---|---|---|---|---|---|---|
| TG-oil | 260.8 | 9.9 | 0.2 | 4.5 | 147.17 | 1.9 | 72.8 | 5.6 | 5.3 | 196.8 |
| PL-1 | 289.9 | 10.9 | 0.1 | 4.2 | 115.07 | 1.4 | 54.7 | 4.3 | 4.5 | 170.1 |
| PL-2 | 232.6 | 2.1 | 0.6 | 4.2 | 122.38 | 1.2 | 57.4 | 4.4 | 0.7 | 175.9 |
| Control | 288.8 | 4.4 | | 3.5 | 181.60 | 0.1 | 86.8 | 7.3 | 0.5 | 213.1 |

TABLE 8

Fatty acid profile of the phospholipids isolated from the adipose tissue (mmol/g lipids).

| | 18:1 | 18:2 | 18:3 n3 | 20:3 | ARA | EPA | 22:4 | 22:5 n6 | 22:5 n3 | DHA |
|---|---|---|---|---|---|---|---|---|---|---|
| TG-oil | 0.7 | 0.9 | 0.04 | 0.04 | 0.45 | 0.10 | 0.0 | 0.0 | 0.0 | 0.17 |
| PL-1 | 0.6 | 0.5 | 0.04 | 0.02 | 0.24 | 0.06 | 0.0 | 0.0 | 0.0 | 0.09 |
| PL-2 | 0.5 | 0.6 | 0.03 | 0.04 | 0.37 | 0.05 | 0.0 | 0.0 | 0.0 | 0.13 |
| Control | 0.5 | 0.4 | 0.04 | 0.03 | 0.57 | 0.01 | 0.0 | 0.0 | 0.0 | 0.04 |

TABLE 9

Fatty acid profile of the phospholipids isolated from the liver (mmol/g lipids).

| | 18:1 | 18:2 | 18:3 n3 | 20:3 | ARA | EPA | 22:4 | 22:5 n6 | 22:5 n3 | DHA |
|---|---|---|---|---|---|---|---|---|---|---|
| TG-oil | 84.2 | 165.4 | 4.4 | 11.5 | 256.9 | 61.6 | 1.7 | 1.69 | 20.5 | 186.5 |
| PL-1 | 107.2 | 227.6 | 4.6 | 11.4 | 287.3 | 67.9 | 2.0 | 1.62 | 29.1 | 207.7 |
| PL-2 | 117.0 | 347.7 | 6.6 | 12.3 | 314.7 | 51.7 | 2.7 | 5.12 | 26.0 | 247.7 |
| Control | 86.7 | 204.4 | 1.6 | 7.6 | 393.6 | 2.8 | 8.0 | 3.41 | 11.0 | 125.9 |

TABLE 10

Fatty acid profile of the phospholipids isolated from the testicles

| nmoles FA/mg lipids | 20:5 | 22:6 | 20:4 | 18:2 | 22:5n3 | 22:5n6 | 22:4 | 18:1 |
|---|---|---|---|---|---|---|---|---|
| TG-oil | 3.18 | 23.00 | 173.10 | 55.30 | 1.55 | 234.24 | 20.50 | 118.11 |
| PL-1 | 3.71 | 31.41 | 227.44 | 82.56 | 2.05 | 317.90 | 28.27 | 143.41 |
| PL-2 | 3.339 | 46.79 | 335.87 | 127.50 | 2.04 | 265.36 | 45.48 | 155.71 |
| Control | 0.430 | 14.08 | 204.27 | 49.39 | 0.36 | 161.20 | 35.70 | 118.18 |

TABLE 11

Fatty acid profile of the phospholipids isolated from the heart.

| nmoles FA/mg lipids | 20:5 | n3 18:3 | 22:6 | 20:4 | 18:2 | 22:5 | 20:3 | 20:3 n9 | 22:4 | 18:1 |
|---|---|---|---|---|---|---|---|---|---|---|
| TG-oil | 35.0 | 6.4 | 286.3 | 240.3 | 877.5 | 4.2 | 5.1 | | 3.2 | 119.6 |
| PL-1 | 27.5 | 6.0 | 261.6 | 205.1 | 754.6 | 3.4 | 4.2 | | 2.6 | 96.3 |
| PL-2 | 20.8 | 4.1 | 331.1 | 227.6 | 570.3 | 7.9 | 5.0 | 1.2 | 4.1 | 115.7 |
| Control | 1.6 | 3.1 | 187.1 | 348.8 | 505.9 | 13.7 | 3.2 | 1.9 | 22.0 | 128.6 |

TABLE 12

Fatty acid profile of the sn-2 position on the phospholipids isolated from the adipose tissue

| sn-2 | EPA | n3 18:3 | DHA | ARA | 18:2 |
|---|---|---|---|---|---|
| TG-oil | 0.06 | 0.03 | 0.09 | 0.24 | 0.57 |
| PL-1 | 0.09 | 0.04 | 0.12 | 0.29 | 0.70 |
| PL-2 | 0.04 | | 0.11 | 0.35 | 0.60 |
| Control | 0.00 | | 0.04 | 0.45 | 0.49 |

TABLE 13

Fatty acid profile of the sn-2 position on the phospholipids isolated from the brain

| sn-2 | EPA | DHA | ARA | 18:2 | 22:5 | 20:3 | 22:4 | 18:1 |
|---|---|---|---|---|---|---|---|---|
| TG-oil | 1.6 | 164.7 | 123.6 | 9.8 | 5.0 | 3.9 | 72.8 | 197.4 |
| PL-1 | 1.3 | 146.3 | 96.5 | 11.6 | 3.7 | 4.1 | 51.8 | 260.2 |
| PL-2 | 1.2 | 173.5 | 120.3 | 3.2 | 4.4 | 4.2 | 57.4 | 223.4 |
| Control | 0.1 | 203.0 | 171.6 | 4.4 | 7.1 | 3.2 | 81.1 | 258.4 |

TABLE 14

Fatty acid profile of the sn-2 position of the phospholipids in the liver.

| sn-2 | 18:4 | 20:5 | n3 18:3 | n6 18:3 | 22:6 | 16:1 | 20:4 | 18:2 | 22:5n3 | 22:5 | 20:3 | 20:3 n9 | 22:4 | 18:1 | 20:2 |
|---|---|---|---|---|---|---|---|---|---|---|---|---|---|---|---|
| TG-oil | 0.5 | 50.2 | 2.3 | 0.3 | 145.3 | 6.9 | 188.6 | 149.5 | 18.6 | 0.9 | 6.4 | 0.5 | 0.9 | 45.1 | 2.7 |
| PL-1 | 0.4 | 60.1 | 2.9 | 0.4 | 176.7 | 0.0 | 235.6 | 193.0 | 24.3 | 1.2 | 8.3 | 0.8 | 1.6 | 77.9 | 2.5 |
| PL-2 | 0.1 | 45.8 | 4.2 | 0.5 | 212.4 | 22.2 | 264.5 | 343.7 | 25.6 | 3.7 | 9.6 | 0.6 | 2.0 | 87.0 | 2.5 |
| Control | 0.0 | 2.5 | 1.3 | 0.4 | 108.6 | 31.7 | 330.9 | 204.4 | 11.0 | 2.7 | 6.0 | 1.2 | 6.4 | 62.6 | 3.7 |

TABLE 15

Fatty acid profile of the sn-2 position of the phospholipids in the testis.

| sn-2 | 20:5 | 22:6 | 20:4 | 18:2 | 22:5 | 22:4 | 18:1 |
|---|---|---|---|---|---|---|---|
| TG-oil | 2.9 | 21.8 | 167.6 | 60.7 | 224.4 | 20.5 | 109.3 |
| PL-1 | 3.4 | 28.4 | 210.7 | 77.2 | 290.6 | 28.2 | 120.3 |
| PL-2 | 2.5 | 41.6 | 304.7 | 110.4 | 244.1 | 45.4 | 137.8 |
| Control | 0.4 | 13.6 | 202.1 | 50.9 | 157.2 | 35.6 | 113.7 |

TABLE 16

Fatty acid profile of the sn-2 position of the phospholipids in the heart

| sn-2 | 20:5 | n3 18:3 | 22:6 | 20:4 | 18:2 | 22:5 | 20:3 | 20:3 n9 | 22:4 | 18:1 |
|---|---|---|---|---|---|---|---|---|---|---|
| TG-oil | 28.6 | 5.3 | 215.4 | 164.9 | 741.7 | 2.9 | 3.2 | | 3.2 | 68.2 |
| PL-1 | 22.2 | 4.3 | 193.4 | 131.5 | 601.8 | 2.1 | 2.2 | | 2.5 | 52.5 |

TABLE 16-continued

Fatty acid profile of the sn-2 position of the phospholipids in the heart

| sn-2 | 20:5 | n3 18:3 | 22:6 | 20:4 | 18:2 | 22:5 | 20:3 | 20:3 n9 | 22:4 | 18:1 |
|---|---|---|---|---|---|---|---|---|---|---|
| PL-2 | 17.6 | 3.4 | 256.7 | 160.4 | 519.5 | 5.7 | 3.2 | 1.2 | 4.1 | 70.0 |
| Control | 1.4 | 1.9 | 163.7 | 283.9 | 467.0 | 8.4 | 2.9 | 1.9 | 21.9 | 96.0 |

Example 4

50 g of soy lecithin from American Lecithin Company Inc (Oxford, Conn., USA), 40 g of TL-IM lipase from Novozymes (Bagsvaerd, Denmark) and 5 g of water (adjusted to pH=8 using NaOH) were mixed in a reaction vessel at 50° C. for 24 hours. Next, 10 g of free fatty acids containing 10% EPA and 50% DHA from Napro Pharma (Brattvaag, Norway) was added, followed by application of vacuum to the reaction vessel. After 72 hours the reaction was terminated and the phospholipid mixture was analyzed using HPLC and GC. The results showed that the relationship between PC/LPC/GPC was 65/35/0, and that the content of EPA and DHA was around 10% and 12%, respectively. Next, 20 g of sardine oil was added to the reaction mixture which comprised of 18% EPA and 12% DHA (relative GC peak area), followed by molecular distillation. The final product contained around 70% acetone insolubles, around 30% triglycerides and traces of free fatty acids.

Example 5

A marine phospholipid composition containing 8.4% EPA and 1.2% DHA was prepared using a crude soybean lecithin as a starting material according to [19]. A marine oil was added to the phospholipid mixture (30% w/w) so that the total level of EPA was 21.9% and for DHA 9.4%. Furthermore, soy lecithin and lyso-phospholipids prepared according to [20] were added to the mixture in variable amounts so that a range of PC/LPC/GPC ratios could be obtained (Table 17). By using this method, all the treatments (MPL1-MPL5) contained exactly the same amount EPA and DHA. Lipid compositions were consumed as a single bolus by adult Sprague-Dawley rats and the appearance of EPA/DHA in blood was measured at different time points from 1 to 12 hours after ingestion. The concentration of EPA/DHA was determined using GC-FID and reported as area percentage. FIGS. 6 and 7 show that composition MPL2 and MPL3 results in the highest concentration of EPA/DHA in plasma after uptake. Comparing the surface area under each curve it is clear that MPL2 and MPL3 demonstrates a higher bioavailability of EPA/DHA than the other composition MPL1, MPL4 and MPL5.

TABLE 17

Hydrolysis profile of the compositions tested

| Treatment | MPL1 | MPL2 | MPL3 | MPL4 | MPL5 |
|---|---|---|---|---|---|
| PC/LPC/GPC | 85/15/0 | 70/30/0 | 55/45/0 | 40/60/0 | 47/37/16 |

Example 6

Marine phospholipids were prepared using either 40% soy PC (American Lecithin Company Inc, Oxford, Conn., USA) (MPL1) or 96% pure soy PC (Phospholipid GmbH, Köln, Germany) (MPL2) according to a method described by others [4]. Fatty acid content and the level of bi-products are shown in table 18. The MPL treatments consisted of a mixture of phospholipids, lyso-phospholipids and glycerol-phospholipids. Looking only at the PC/LPC/GPC relationship, it was 64/33/2 and 42/40/18 for MPL1 and MPL2, respectively. Finally, all three treatments were emulsified into skimmed milk.

TABLE 18

Composition of the phospholipids used in example 2

| Composition | PC/LPC/GPC | 18:2 (n-6) | 18:3 (n-3) | EPA | DHA |
|---|---|---|---|---|---|
| MPL1 | 64/33/2 | 129 mg/g | 9 mg/g | 51 mg/g | 171 mg/g |
| MPL2 | 42/40/18 | 124 mg/g | 9 mg/g | 96 mg/g | 96 mg/g |

18 newly weaned Sprague-Dawley rats were fed the milk emulsions for 1 week. Each rat was placed in its own cage to ensure that they got an even amount of test substance and the milk was consumed by the rat pups ad libitum. After 1 week the experiment was terminated and the rats were decapitated. The animals were kept without food for 24 hours before sampling. Entire livers were collected and frozen immediately using liquid nitrogen (stored at −65° C.). Total RNA was isolated from the liver samples according to the Quiagen Rnaesy Midi Kit Protocol. The RNA samples were quantified and quality measured by NanoDrop and Bioanalyzer. The isolated RNA was hybridized onto a gene chip RAE230 2.0 from Affymetrix (Santa Clara, Calif., USA). The expression level of each gene was measured using an Affymetrix GeneChip 3000 7G scanner. The results were suitable for all chips except 2 and they were excluded from the trial. Using statistical tools a list of genes expressed differentially between MPL1 versus MPL2 (Table 3) was obtained. The results are based on (log) probe set summary expression measures, computed by RMA, and linear models are fitted using Empirical Bayes methods for borrowing strength across genes (using the Limma package in R). The p-value are adjusted for multiple testing using the Benjamini-Hochberg-method, controlling the False Discovery Rate (FDR), where FDR=the proportion of null-hypotheses of no DE that are falsely rejected.

It was observed that MPL1 and MPL2 are biologically different compounds due to the fact that over 40 genes were differentially expressed (table 19).

TABLE 19

| Gene-name | t | p-value | FDR | SLR | Fold change | Affy Fold.change | df |
|---|---|---|---|---|---|---|---|
| Wiskott-Aldrich syndrome-like | 8.35 | 0.00000 | 0.00261 | 1.02 | 2.02 | 2.02 | 14 |
| Similar to osteoclast inhibitory lectin | 7.40 | 0.00000 | 0.00392 | 1.49 | 2.80 | 2.80 | 14 |
| neuron-glia-CAM-related cell adhesion molecule | −7.14 | 0.00000 | 0.00392 | −0.55 | 0.68 | −1.46 | 14 |
| dehydrodolichyl diphosphate synthase (predicted) | 7.09 | 0.00000 | 0.00392 | 0.57 | 1.49 | 1.49 | 14 |
| casein kinase II, alpha 1 polypeptide | 7.05 | 0.00000 | 0.00392 | 1.47 | 2.77 | 2.77 | 14 |
| similar to cisplatin resistance-associated overexpressed protein (predicted) | 7.03 | 0.00000 | 0.00392 | 0.94 | 1.92 | 1.92 | 14 |
| similar to Retinoblastoma-binding protein 2 (RBBP-2) | 7.01 | 0.00000 | 0.00392 | 0.67 | 1.59 | 1.59 | 14 |
| serine/threonine kinase 25 (STE20 homolog, yeast) | 6.90 | 0.00000 | 0.00392 | 0.43 | 1.35 | 1.35 | 14 |
| Delangin (predicted) | 6.89 | 0.00000 | 0.00392 | 0.69 | 1.61 | 1.61 | 14 |
| similar to Hypothetical protein MGC30714 | −6.80 | 0.00000 | 0.00401 | −0.40 | 0.76 | −1.32 | 14 |
| myeloid/lymphoid or mixed-lineage leukemia 5 (trithorax homolog, Drosophila) (predicted) | 6.77 | 0.00000 | 0.00401 | 0.68 | 1.60 | 1.60 | 14 |
| Radixin | 6.76 | 0.00000 | 0.00401 | 0.74 | 1.67 | 1.67 | 14 |
| similar to myocyte enhancer factor 2C | 6.70 | 0.00000 | 0.00420 | 0.60 | 1.52 | 1.52 | 14 |
| WD repeat and FYVE domain containing 1 (predicted) | 6.64 | 0.00000 | 0.00443 | 0.80 | 1.74 | 1.74 | 14 |
| similar to Retinoblastoma-binding protein 2 (RBBP-2) | 6.55 | 0.00000 | 0.00509 | 0.87 | 1.82 | 1.82 | 14 |
| zinc and ring finger 1 (predicted) | −6.50 | 0.00000 | 0.00528 | −0.51 | 0.70 | −1.42 | 14 |
| pumilio 1 (Drosophila) (predicted) | 6.45 | 0.00000 | 0.00535 | 0.59 | 1.51 | 1.51 | 14 |
| leukocyte receptor cluster (LRC) member 8 (predicted) | 6.44 | 0.00000 | 0.00535 | 1.06 | 2.08 | 2.08 | 14 |
| Similar to collapsin response mediator protein-2A | −6.40 | 0.00000 | 0.00542 | −0.52 | 0.70 | −1.43 | 14 |
| SWI/SNF related, matrix associated, actin dependent regulator of chromatin, subfamily a, member 4 | 6.37 | 0.00000 | 0.00542 | 0.74 | 1.67 | 1.67 | 14 |
| B-cell CLL/lymphoma 7C (predicted) | 6.37 | 0.00000 | 0.00542 | 0.51 | 1.42 | 1.42 | 14 |
| synaptic vesicle glycoprotein 2b | 6.33 | 0.00000 | 0.00568 | 0.97 | 1.96 | 1.96 | 14 |
| leptin receptor overlapping transcript | −6.31 | 0.00000 | 0.00570 | −0.58 | 0.67 | −1.50 | 14 |
| Transcribed locus | 6.22 | 0.00001 | 0.00658 | 0.44 | 1.36 | 1.36 | 14 |
| similar to mKIAA1321 protein | 6.20 | 0.00001 | 0.00658 | 0.99 | 1.99 | 1.99 | 14 |
| retinol binding protein 2, cellular | 6.18 | 0.00001 | 0.00660 | 0.59 | 1.51 | 1.51 | 14 |
| similar to Safb2 protein | 6.16 | 0.00001 | 0.00660 | 0.62 | 1.53 | 1.53 | 14 |
| similar to Zbtb20 protein | 6.15 | 0.00001 | 0.00660 | 0.49 | 1.40 | 1.40 | 14 |
| phosphofructokinase, liver, B-type | 6.13 | 0.00001 | 0.00665 | 0.67 | 1.60 | 1.60 | 14 |
| Transcription elongation factor B (SIII), polypeptide 3 | 6.10 | 0.00001 | 0.00668 | 0.43 | 1.35 | 1.35 | 14 |
| Echinoderm microtubule associated protein like 4 (predicted) | 6.10 | 0.00001 | 0.00668 | 1.00 | 2.00 | 2.00 | 14 |
| DNA topoisomerase I, mitochondrial | 6.08 | 0.00001 | 0.00678 | 0.61 | 1.53 | 1.53 | 14 |
| ectonucleoside triphosphate diphosphohydrolase 5 | 5.96 | 0.00001 | 0.00849 | 0.74 | 1.67 | 1.67 | 14 |
| nuclear factor I/X | 5.94 | 0.00001 | 0.00859 | 0.65 | 1.57 | 1.57 | 14 |
| WW domain binding protein 4 | 5.90 | 0.00001 | 0.00914 | 0.58 | 1.50 | 1.50 | 14 |
| Acetyl-coenzyme A acetyltransferase 1 | 5.84 | 0.00001 | 0.00967 | 0.69 | 1.61 | 1.61 | 14 |
| similar to THO complex 2 | 5.84 | 0.00001 | 0.00967 | 0.74 | 1.67 | 1.67 | 14 |

List of genes differentially expressed (DE) by MPL1 versus MPL2. The list is sorted according to increasing p-values. SLR: Estimated signal log-ratio (<0: down regulated gene, >0: up regulated gene). Fold change: Estimated fold change corresponding to the parameter (<1: down regulated gene, >1: up regulated gene). Affy fold change: Estimated fold change using the Affymetrix definition (<−1: down regulated gene, >1: up regulated gene). df: Degrees of freedom (=number of arrays − number of estimated parameters).

MPL2 regulates 401 genes versus the control (table 20). A number of genes listed are involved maintenance of the cell, in transcription and protein synthesis as well as signaling pathways. Others are involved in regulation of metabolism and the inflammatory response such as Tnf receptor-associated factor 6 (Traf6_predicted) (fold change of 0.53), guanine nucleotide binding protein alpha inhibiting 2 (Gnai2) (fold change of 0.6, gamma-butyrobetaine hydroxylase (Bbox1) (fold change of 1.32), monoglyceride lipase (Mgll) (fold change 0.52), nuclear NF-kappaB activating protein (fold change 0.65) and CCAAT/enhancer binding protein (C/EBP) (fold change of 0.66). The data listed in table 4 show that a omega-3 rich phospholipid with an EPA/DHA ratio of 2:1 behaves differently compared to placebo. A phospholipid composition with an EPA/DHA ratio of 1:1 did not show any difference versus placebo on gene expression. Consequently, the EPA/DHA ratio is important and should preferably be 2:1.

TABLE 20

| Gene-ID | Gene name | t | p-value | FDR | SLR | Fold change | Affy Fold.change | df |
|---|---|---|---|---|---|---|---|---|
| 1367588_a_at | ribosomal protein L13A | −5.22 | 0.00005 | 0.00568 | −0.44 | 0.74 | −1.36 | 14 |
| 1367844_at | guanine nucleotide binding protein, alpha inhibiting 2 | −5.47 | 0.00003 | 0.00417 | −0.54 | 0.69 | −1.46 | 14 |
| 1367958_at | abl-interactor 1 | −6.42 | 0.00000 | 0.00119 | −0.69 | 0.62 | −1.62 | 14 |
| 1367971_at | protein tyrosine phosphatase 4a2 | −6.01 | 0.00001 | 0.00190 | −0.36 | 0.78 | −1.28 | 14 |
| 1368057_at | ATP-binding cassette, sub-family D (ALD), member 3 | −5.06 | 0.00007 | 0.00688 | −0.54 | 0.69 | −1.45 | 14 |
| 1368405_at | v-ral simian leukemia viral oncogene homolog A (ras related) | −4.86 | 0.00011 | 0.00913 | −0.44 | 0.74 | −1.36 | 14 |
| 1368646_at | mitogen-activated protein kinase 9 | 4.98 | 0.00008 | 0.00772 | 0.70 | 1.62 | 1.62 | 14 |
| 1368649_at | dyskeratosis congenita 1, dyskerin | −6.73 | 0.00000 | 0.00080 | −0.53 | 0.69 | −1.44 | 14 |
| 1368662_at | ring finger protein 39 | −7.01 | 0.00000 | 0.00053 | −0.61 | 0.66 | −1.52 | 14 |
| 1368703_at | enigma homolog | −5.38 | 0.00003 | 0.00450 | −0.76 | 0.59 | −1.70 | 14 |
| 1368824_at | caldesmon 1 | −7.18 | 0.00000 | 0.00043 | −1.00 | 0.50 | −2.00 | 14 |
| 1368841_at | transcription factor 4 | −4.94 | 0.00009 | 0.00828 | −0.38 | 0.77 | −1.31 | 14 |
| 1368867_at | GERp95 | −7.83 | 0.00000 | 0.00019 | −0.85 | 0.56 | −1.80 | 14 |
| 1369094_a_at | protein tyrosine phosphatase, receptor type, D | −7.22 | 0.00000 | 0.00042 | −0.97 | 0.51 | −1.96 | 14 |
| 1369127_a_at | prostaglandin F receptor | 4.85 | 0.00011 | 0.00921 | 0.45 | 1.37 | 1.37 | 14 |
| 1369174_at | SMAD, mothers against DPP homolog 1 (Drosophila) | −5.19 | 0.00005 | 0.00581 | −0.38 | 0.77 | −1.30 | 14 |
| 1369227_at | Choroidermia | 5.04 | 0.00007 | 0.00718 | 0.47 | 1.39 | 1.39 | 14 |
| 1369249_at | progressive ankylosis homolog (mouse) | 5.36 | 0.00004 | 0.00467 | 0.48 | 1.39 | 1.39 | 14 |
| 1369501_at | zinc finger protein 260 | 5.17 | 0.00005 | 0.00595 | 0.41 | 1.33 | 1.33 | 14 |
| 1369517_at | pleckstrin homology, Sec7 and coiled/coil domains 1 | 4.93 | 0.00009 | 0.00829 | 0.48 | 1.40 | 1.40 | 14 |
| 1369546_at | butyrobetaine (gamma), 2-oxoglutarate dioxygenase 1 (gamma-butyrobetaine hydroxylase) | 4.96 | 0.00009 | 0.00811 | 0.40 | 1.32 | 1.32 | 14 |
| 1369628_at | synaptic vesicle glycoprotein 2b | −7.20 | 0.00000 | 0.00042 | −1.11 | 0.46 | −2.15 | 14 |
| 1369689_at | N-ethylmaleimide sensitive fusion protein | 6.22 | 0.00001 | 0.00155 | 0.66 | 1.58 | 1.58 | 14 |
| 1369736_at | epithelial membrane protein 1 | 5.74 | 0.00002 | 0.00286 | 0.62 | 1.54 | 1.54 | 14 |
| 1369775_at | nuclear ubiquitous casein kinase and cyclin-dependent kinase substrate | −7.56 | 0.00000 | 0.00027 | −0.79 | 0.58 | −1.73 | 14 |
| 1370184_at | cofilin 1 | −6.07 | 0.00001 | 0.00178 | −0.38 | 0.77 | −1.30 | 14 |
| 1370260_at | adducin 3 (gamma) | −5.50 | 0.00003 | 0.00399 | −0.76 | 0.59 | −1.70 | 14 |
| 1370328_at | Dickkopf homolog 3 (Xenopus laevis) | 4.80 | 0.00012 | 0.00964 | 0.59 | 1.51 | 1.51 | 14 |
| 1370717_at | AP1 gamma subunit binding protein 1 | 6.00 | 0.00001 | 0.00192 | 0.58 | 1.50 | 1.50 | 14 |
| 1370831_at | monoglyceride lipase | −5.47 | 0.00003 | 0.00414 | −0.94 | 0.52 | −1.92 | 14 |
| 1370901_at | similar to hypothetical protein MGC36831 (predicted) | −4.83 | 0.00012 | 0.00948 | −0.34 | 0.79 | −1.27 | 14 |
| 1370946_at | nuclear factor I/X | −10.64 | 0.00000 | 0.00002 | −1.17 | 0.45 | −2.25 | 14 |
| 1370949_at | myristoylated alanine rich protein kinase C substrate | −7.58 | 0.00000 | 0.00026 | −1.17 | 0.44 | −2.26 | 14 |
| 1370993_at | laminin, gamma 1 | 6.13 | 0.00001 | 0.00171 | 0.63 | 1.54 | 1.54 | 14 |
| 1371034_at | one cut domain, family member 1 | −5.65 | 0.00002 | 0.00327 | −1.77 | 0.29 | −3.40 | 14 |
| 1371059_at | protein kinase, cAMP-dependent, regulatory, type 2, alpha | 5.24 | 0.00005 | 0.00556 | 0.48 | 1.40 | 1.40 | 14 |
| 1371345_at | methyl-CpG binding domain protein 3 (predicted) | −5.32 | 0.00004 | 0.00491 | −0.34 | 0.79 | −1.27 | 14 |
| 1371361_at | similar to tensin | −7.21 | 0.00000 | 0.00042 | −0.60 | 0.66 | −1.51 | 14 |
| 1371394_x_at | similar to Ab2-143 | −5.11 | 0.00006 | 0.00645 | −0.63 | 0.64 | −1.55 | 14 |
| 1371397_at | nitric oxide synthase interacting protein (predicted) | −5.53 | 0.00002 | 0.00383 | −0.34 | 0.79 | −1.26 | 14 |
| 1371428_at | | −5.76 | 0.00001 | 0.00276 | −0.37 | 0.77 | −1.29 | 14 |
| 1371430_at | dystroglycan 1 | −5.46 | 0.00003 | 0.00417 | −0.62 | 0.65 | −1.53 | 14 |
| 1371432_at | | −4.95 | 0.00009 | 0.00811 | −0.36 | 0.78 | −1.28 | 14 |
| 1371452_at | bone marrow stromal cell-derived ubiquitin-like protein | −5.05 | 0.00007 | 0.00705 | −0.46 | 0.73 | −1.37 | 14 |
| 1371573_at | ribosomal protein L36a (predicted) | −5.90 | 0.00001 | 0.00221 | −0.40 | 0.76 | −1.32 | 14 |
| 1371589_at | Ubiquitin-Like 5 Protein | −5.28 | 0.00004 | 0.00518 | −0.57 | 0.68 | −1.48 | 14 |
| 1371590_s_at | Ubiquitin-Like 5 Protein | −4.94 | 0.00009 | 0.00829 | −0.39 | 0.76 | −1.31 | 14 |
| 1371779_at | sorting nexin 6 (predicted) | 5.64 | 0.00002 | 0.00329 | 0.63 | 1.55 | 1.55 | 14 |

TABLE 20-continued

| Gene-ID | Gene name | t | p-value | FDR | SLR | Fold change | Affy Fold.change | df |
|---|---|---|---|---|---|---|---|---|
| 1371826_at | Transcribed locus | −5.58 | 0.00002 | 0.00359 | −0.48 | 0.72 | −1.39 | 14 |
| 1371896_at | growth arrest and DNA-damage-inducible, gamma interacting protein 1 (predicted) | −6.02 | 0.00001 | 0.00189 | −0.43 | 0.74 | −1.35 | 14 |
| 1371918_at | CD99 | −5.35 | 0.00004 | 0.00476 | −0.37 | 0.77 | −1.29 | 14 |
| 1372057_at | CDNA clone MGC: 124976 IMAGE: 7110947 | −6.12 | 0.00001 | 0.00173 | −0.38 | 0.77 | −1.30 | 14 |
| 1372137_at | biogenesis of lysosome-related organelles complex-1, subunit 1 (predicted) | −6.03 | 0.00001 | 0.00187 | −0.41 | 0.75 | −1.32 | 14 |
| 1372142_at | arsA arsenite transporter, ATP-binding, homolog 1 (bacterial) (predicted) | −4.93 | 0.00009 | 0.00829 | −0.37 | 0.77 | −1.30 | 14 |
| 1372236_at | Similar to Caspase recruitment domain protein 4 | −4.90 | 0.00010 | 0.00871 | −0.36 | 0.78 | −1.29 | 14 |
| 1372469_at | Transcribed locus | −4.84 | 0.00011 | 0.00945 | −0.36 | 0.78 | −1.28 | 14 |
| 1372697_at | mitochondrial ribosomal protein S15 | −5.70 | 0.00002 | 0.00299 | −0.58 | 0.67 | −1.49 | 14 |
| 1373031_at | tripartite motif protein 8 (predicted) | −5.13 | 0.00006 | 0.00628 | −0.44 | 0.74 | −1.36 | 14 |
| 1373105_at | interleukin 1 receptor-like 1 ligand (predicted) | −5.01 | 0.00008 | 0.00742 | −0.37 | 0.77 | −1.30 | 14 |
| 1373135_at | similar to hypothetical protein MGC2744 | −5.30 | 0.00004 | 0.00503 | −0.55 | 0.68 | −1.46 | 14 |
| 1373206_at | similar to FAD104 (predicted) | 6.73 | 0.00000 | 0.00080 | 0.64 | 1.56 | 1.56 | 14 |
| 1373303_at | similar to mKIAA3013 protein | −5.28 | 0.00004 | 0.00514 | −0.48 | 0.72 | −1.39 | 14 |
| 1373347_at | DMT1-associated protein | −6.18 | 0.00001 | 0.00162 | −0.73 | 0.60 | −1.66 | 14 |
| 1373378_at | ATP/GTP binding protein 1 (predicted) | 5.39 | 0.00003 | 0.00449 | 0.51 | 1.42 | 1.42 | 14 |
| 1373804_at | Forkhead box P1 (predicted) | −5.28 | 0.00004 | 0.00518 | −0.59 | 0.66 | −1.51 | 14 |
| 1373885_at | chromobox homolog 5 (Drosophila HP1a) (predicted) | −5.94 | 0.00001 | 0.00208 | −1.04 | 0.48 | −2.06 | 14 |
| 1374002_at | | −6.78 | 0.00000 | 0.00074 | −0.86 | 0.55 | −1.82 | 14 |
| 1374283_at | fetal Alzheimer antigen (predicted) | −7.44 | 0.00000 | 0.00032 | −0.74 | 0.60 | −1.67 | 14 |
| 1374425_at | transducin-like enhancer of split 1, homolog of Drosophila E(spl) (predicted) | −4.91 | 0.00010 | 0.00849 | −0.40 | 0.76 | −1.32 | 14 |
| 1374509_at | Similar to RIKEN cDNA 1110018O08 | −5.62 | 0.00002 | 0.00337 | −0.47 | 0.72 | −1.39 | 14 |
| 1374511_at | | 5.60 | 0.00002 | 0.00345 | 0.55 | 1.47 | 1.47 | 14 |
| 1374657_at | Transcribed locus | −4.88 | 0.00010 | 0.00890 | −0.34 | 0.79 | −1.27 | 14 |
| 1374733_at | symplekin (predicted) | −5.04 | 0.00007 | 0.00716 | −0.36 | 0.78 | −1.28 | 14 |
| 1374772_at | similar to Chromosome 13 open reading frame 21 | 5.18 | 0.00005 | 0.00581 | 0.46 | 1.38 | 1.38 | 14 |
| 1374837_at | B-cell CLL/lymphoma 7C (predicted) | −8.92 | 0.00000 | 0.00006 | −0.71 | 0.61 | −1.63 | 14 |
| 1374851_at | similar to RIKEN cDNA 2810405O22 (predicted) | −4.89 | 0.00010 | 0.00879 | −0.39 | 0.76 | −1.31 | 14 |
| 1374852_at | hypothetical LOC362592 | −5.20 | 0.00005 | 0.00579 | −0.37 | 0.78 | −1.29 | 14 |
| 1375214_at | UDP-N-acetyl-alpha-D-galactosamine: polypeptide N-acetylgalactosaminyltransferase 2 (predicted) | −5.31 | 0.00004 | 0.00500 | −0.58 | 0.67 | −1.50 | 14 |
| 1375335_at | heat shock 90 kDa protein 1, beta | −5.26 | 0.00004 | 0.00538 | −0.55 | 0.68 | −1.46 | 14 |
| 1375396_at | pumilio 1 (Drosophila) (predicted) | −10.05 | 0.00000 | 0.00003 | −0.92 | 0.53 | −1.89 | 14 |
| 1375421_a_at | praja 2, RING-H2 motif containing | −6.51 | 0.00000 | 0.00102 | −0.60 | 0.66 | −1.52 | 14 |
| 1375453_at | | −12.32 | 0.00000 | 0.00000 | −1.02 | 0.49 | −2.02 | 14 |
| 1375469_at | SWI/SNF related, matrix associated, actin dependent regulator of chromatin, subfamily a, member 4 | −7.97 | 0.00000 | 0.00017 | −0.93 | 0.53 | −1.90 | 14 |
| 1375533_at | vestigial like 4 (Drosophila) (predicted) | −5.30 | 0.00004 | 0.00505 | −0.61 | 0.66 | −1.52 | 14 |
| 1375548_at | similar to RIKEN cDNA 4732418C07 (predicted) | −5.64 | 0.00002 | 0.00328 | −0.58 | 0.67 | −1.50 | 14 |
| 1375621_at | | −7.05 | 0.00000 | 0.00051 | −0.96 | 0.51 | −1.95 | 14 |
| 1375632_at | similar to 60S ribosomal protein L38 | −4.85 | 0.00011 | 0.00921 | −0.29 | 0.82 | −1.22 | 14 |
| 1375650_at | bromodomain containing 4 (predicted) | −6.64 | 0.00000 | 0.00088 | −0.48 | 0.71 | −1.40 | 14 |
| 1375658_at | Transcribed locus | −5.00 | 0.00008 | 0.00756 | −0.44 | 0.74 | −1.35 | 14 |

TABLE 20-continued

| Gene-ID | Gene name | t | p-value | FDR | SLR | Fold change | Affy Fold.change | df |
|---|---|---|---|---|---|---|---|---|
| 1375696_at | interferon (alpha and beta) receptor 1 (predicted) | 4.81 | 0.00012 | 0.00958 | 0.59 | 1.51 | 1.51 | 14 |
| 1375703_at | myeloid/lymphoid or mixed-lineage leukemia 5 (trithorax homolog, *Drosophila*) (predicted) | −10.20 | 0.00000 | 0.00003 | −1.02 | 0.49 | −2.03 | 14 |
| 1375706_at | | −5.01 | 0.00008 | 0.00743 | −0.49 | 0.71 | −1.40 | 14 |
| 1375763_at | similar to 2700008B19Rik protein | −7.08 | 0.00000 | 0.00050 | −0.54 | 0.69 | −1.45 | 14 |
| 1375958_at | | −5.13 | 0.00006 | 0.00628 | −0.65 | 0.64 | −1.57 | 14 |
| 1376059_at | | 5.33 | 0.00004 | 0.00483 | 0.35 | 1.28 | 1.28 | 14 |
| 1376256_at | WD repeat and FYVE domain containing 1 (predicted) | −9.16 | 0.00000 | 0.00005 | −1.10 | 0.47 | −2.15 | 14 |
| 1376299_at | similar to Retinoblastoma-binding protein 2 (RBBP-2) | −9.22 | 0.00000 | 0.00005 | −0.89 | 0.54 | −1.85 | 14 |
| 1376450_at | transmembrane protein 5 (predicted) | −6.26 | 0.00001 | 0.00147 | −0.55 | 0.68 | −1.46 | 14 |
| 1376523_at | AT rich interactive domain 4A (Rbp1 like) (predicted) | −5.53 | 0.00002 | 0.00383 | −0.77 | 0.59 | −1.70 | 14 |
| 1376524_at | hypothetical protein Dd25 | −6.69 | 0.00000 | 0.00082 | −0.66 | 0.63 | −1.58 | 14 |
| 1376532_at | similar to FAD104 (predicted) | 6.06 | 0.00001 | 0.00178 | 0.56 | 1.47 | 1.47 | 14 |
| 1376728_at | Transcribed locus | −4.80 | 0.00012 | 0.00966 | −0.35 | 0.78 | −1.27 | 14 |
| 1376917_at | zinc finger protein 292 | −5.21 | 0.00005 | 0.00571 | −0.66 | 0.63 | −1.58 | 14 |
| 1376982_at | Transcribed locus | −5.49 | 0.00003 | 0.00405 | −0.45 | 0.73 | −1.37 | 14 |
| 1377105_at | | −6.97 | 0.00000 | 0.00056 | −0.89 | 0.54 | −1.85 | 14 |
| 1377302_a_at | methylmalonic aciduria (cobalamin deficiency) type A (predicted) | −5.10 | 0.00006 | 0.00660 | −0.52 | 0.70 | −1.43 | 14 |
| 1377524_at | similar to CG18661-PA (predicted) | −5.36 | 0.00003 | 0.00465 | −0.43 | 0.74 | −1.35 | 14 |
| 1377663_at | ras homolog gene family, member E | −5.00 | 0.00008 | 0.00756 | −0.87 | 0.55 | −1.82 | 14 |
| 1377683_at | similar to hypothetical protein FLJ13045 (predicted) | −6.63 | 0.00000 | 0.00088 | −0.56 | 0.68 | −1.47 | 14 |
| 1377728_at | LOC499567 | −5.45 | 0.00003 | 0.00419 | −1.03 | 0.49 | −2.04 | 14 |
| 1377766_at | Transcribed locus | 4.80 | 0.00012 | 0.00964 | 0.37 | 1.29 | 1.29 | 14 |
| 1377899_at | similar to RIKEN cDNA 2810025M15 (predicted) | −4.99 | 0.00008 | 0.00760 | −0.46 | 0.73 | −1.38 | 14 |
| 1377906_at | DEAH (Asp-Glu-Ala-His) box polypeptide 36 (predicted) | −4.82 | 0.00012 | 0.00950 | −0.73 | 0.60 | −1.66 | 14 |
| 1377914_at | serine/arginine repetitive matrix 1 (predicted) | −6.41 | 0.00000 | 0.00120 | −0.98 | 0.51 | −1.97 | 14 |
| 1378155_at | similar to KIAA1096 protein | −5.68 | 0.00002 | 0.00313 | −0.89 | 0.54 | −1.86 | 14 |
| 1378163_at | Transcribed locus | −4.86 | 0.00011 | 0.00913 | −0.78 | 0.58 | −1.71 | 14 |
| 1378170_at | Transcribed locus | −5.00 | 0.00008 | 0.00756 | −0.92 | 0.53 | −1.90 | 14 |
| 1378194_a_at | rap2 interacting protein x | −4.82 | 0.00012 | 0.00950 | −0.72 | 0.61 | −1.65 | 14 |
| 1378361_at | chromodomain helicase DNA binding protein 7 (predicted) | −7.32 | 0.00000 | 0.00039 | −0.73 | 0.60 | −1.66 | 14 |
| 1378453_at | | −4.84 | 0.00011 | 0.00938 | −0.74 | 0.60 | −1.66 | 14 |
| 1378504_at | Insulin-like growth factor I mRNA, 3' end of mRNA | −5.41 | 0.00003 | 0.00440 | −0.96 | 0.51 | −1.95 | 14 |
| 1378786_at | Transcribed locus, weakly similar to NP_780607.2 hypothetical protein LOC109050 [*Mus musculus*] | 4.89 | 0.00010 | 0.00879 | 0.33 | 1.25 | 1.25 | 14 |
| 1379062_at | similar to Expressed sequence AU019823 | −6.60 | 0.00000 | 0.00090 | −1.08 | 0.47 | −2.12 | 14 |
| 1379073_at | Similar to RIKEN cDNA 2310067G05 | −5.51 | 0.00003 | 0.00394 | −0.49 | 0.71 | −1.40 | 14 |
| 1379101_at | DEAH (Asp-Glu-Ala-His) box polypeptide 36 (predicted) | −5.55 | 0.00002 | 0.00375 | −0.87 | 0.55 | −1.82 | 14 |
| 1379112_at | AT rich interactive domain 4A (Rbp1 like) (predicted) | −5.70 | 0.00002 | 0.00299 | −0.44 | 0.74 | −1.35 | 14 |
| 1379232_at | TBC1D12: TBC1 domain family, member 12 (predicted) | −6.98 | 0.00000 | 0.00056 | −1.40 | 0.38 | −2.63 | 14 |
| 1379330_s_at | CDNA clone IMAGE: 7316839 | −4.80 | 0.00012 | 0.00967 | −0.36 | 0.78 | −1.28 | 14 |
| 1379332_at | Transcribed locus, strongly similar to XP_417265.1 PREDICTED: similar to F-box-WD40 repeat protein 6 [*Gallus gallus*] | −4.88 | 0.00010 | 0.00886 | −0.61 | 0.66 | −1.52 | 14 |
| 1379399_at | similar to cDNA sequence BC016188 (predicted) | −5.37 | 0.00003 | 0.00459 | −0.42 | 0.75 | −1.34 | 14 |

TABLE 20-continued

| Gene-ID | Gene name | t | p-value | FDR | SLR | Fold change | Affy Fold.change | df |
|---|---|---|---|---|---|---|---|---|
| 1379457_at | neural precursor cell expressed, developmentally down-regulated gene 1 (predicted) | −5.39 | 0.00003 | 0.00449 | −0.56 | 0.68 | −1.48 | 14 |
| 1379469_at | similar to transducin (beta)-like 1 X-linked | −6.23 | 0.00001 | 0.00153 | −0.91 | 0.53 | −1.88 | 14 |
| 1379485_at | eukaryotic translation initiation factor 3, subunit 10 (theta) (predicted) | −7.08 | 0.00000 | 0.00050 | −1.68 | 0.31 | −3.21 | 14 |
| 1379571_at | plakophilin 4 (predicted) | −5.42 | 0.00003 | 0.00436 | −0.74 | 0.60 | −1.67 | 14 |
| 1379578_at | similar to Zbtb20 protein | −8.89 | 0.00000 | 0.00006 | −0.71 | 0.61 | −1.63 | 14 |
| 1379662_a_at | SNF related kinase | 4.93 | 0.00009 | 0.00829 | 0.36 | 1.29 | 1.29 | 14 |
| 1379715_at | similar to CG9346-PA (predicted) | −4.93 | 0.00009 | 0.00829 | −0.71 | 0.61 | −1.63 | 14 |
| 1379826_at | similar to hypothetical protein MGC31967 | −5.95 | 0.00001 | 0.00208 | −0.62 | 0.65 | −1.54 | 14 |
| 1380008_at | similar to Neurofilament triplet H protein (200 kDa neurofilament protein) (Neurofilament heavy polypeptide) (NF-H) (predicted) | −5.11 | 0.00006 | 0.00645 | −0.60 | 0.66 | −1.52 | 14 |
| 1380060_at | DNA topoisomerase I, mitochondrial | −5.23 | 0.00005 | 0.00566 | −0.53 | 0.69 | −1.44 | 14 |
| 1380062_at | membrane protein, palmitoylated 6 (MAGUK p55 subfamily member 6) (predicted) | −6.88 | 0.00000 | 0.00065 | −0.75 | 0.59 | −1.68 | 14 |
| 1380166_at | Similar to hypothetical protein FLJ12056 | 5.63 | 0.00002 | 0.00333 | 0.34 | 1.27 | 1.27 | 14 |
| 1380371_at | delangin (predicted) | −9.37 | 0.00000 | 0.00005 | −0.94 | 0.52 | −1.91 | 14 |
| 1380446_at | myeloid/lymphoid or mixed-lineage leukemia (trithorax homolog, Drosophila); translocated to, 10 (predicted) | −5.00 | 0.00008 | 0.00756 | −0.62 | 0.65 | −1.54 | 14 |
| 1380503_at | hypothetical LOC305452 (predicted) | −6.07 | 0.00001 | 0.00178 | −0.62 | 0.65 | −1.53 | 14 |
| 1380728_at | Similar to collapsin response mediator protein-2A | 6.09 | 0.00001 | 0.00178 | 0.49 | 1.41 | 1.41 | 14 |
| 1381469_a_at | PERQ amino acid rich, with GYF domain 1 (predicted) | −5.49 | 0.00003 | 0.00405 | −0.51 | 0.70 | −1.43 | 14 |
| 1381525_at | | −4.82 | 0.00012 | 0.00952 | −0.41 | 0.75 | −1.33 | 14 |
| 1381542_at | UBX domain containing 2 (predicted) | −6.15 | 0.00001 | 0.00171 | −0.83 | 0.56 | −1.78 | 14 |
| 1381548_at | golgi phosphoprotein 4 (predicted) | −5.81 | 0.00001 | 0.00256 | −0.69 | 0.62 | −1.61 | 14 |
| 1381567_at | hypothetical LOC294390 (predicted) | 4.97 | 0.00008 | 0.00800 | 0.36 | 1.29 | 1.29 | 14 |
| 1381764_s_at | ring finger protein 126 (predicted) | −5.54 | 0.00002 | 0.00382 | −0.51 | 0.70 | −1.42 | 14 |
| 1381809_at | ankyrin repeat domain 11 (predicted) | −5.94 | 0.00001 | 0.00209 | −1.11 | 0.46 | −2.17 | 14 |
| 1381829_at | | −6.27 | 0.00000 | 0.00145 | −1.07 | 0.48 | −2.10 | 14 |
| 1381878_at | ubinuclein 1 (predicted) | −5.82 | 0.00001 | 0.00252 | −1.18 | 0.44 | −2.26 | 14 |
| 1381958_at | similar to mKIAA0259 protein | −6.90 | 0.00000 | 0.00062 | −1.27 | 0.41 | −2.42 | 14 |
| 1382000_at | | 4.82 | 0.00012 | 0.00950 | 0.41 | 1.33 | 1.33 | 14 |
| 1382009_at | Transcribed locus | −5.39 | 0.00003 | 0.00449 | −0.69 | 0.62 | −1.62 | 14 |
| 1382027_at | LOC498010 | −6.28 | 0.00000 | 0.00144 | −0.76 | 0.59 | −1.70 | 14 |
| 1382056_at | similar to splicing factor p54 | −8.13 | 0.00000 | 0.00016 | −0.97 | 0.51 | −1.96 | 14 |
| 1382109_at | nuclear NF-kappaB activating protein | −5.83 | 0.00001 | 0.00250 | −0.62 | 0.65 | −1.53 | 14 |
| 1382155_at | | 6.37 | 0.00000 | 0.00126 | 0.58 | 1.50 | 1.50 | 14 |
| 1382193_at | Transcribed locus | −6.07 | 0.00001 | 0.00178 | −1.42 | 0.37 | −2.67 | 14 |
| 1382306_at | Ariadne ubiquitin-conjugating enzyme E2 binding protein homolog 1 (Drosophila) (predicted) | 6.59 | 0.00000 | 0.00090 | 0.59 | 1.50 | 1.50 | 14 |
| 1382307_at | protein phosphatase 1, regulatory (inhibitor) subunit 12A | −4.79 | 0.00013 | 0.00976 | −0.47 | 0.72 | −1.39 | 14 |
| 1382358_at | Similar to SRY (sex determining region Y)-box 5 isoform a | −5.34 | 0.00004 | 0.00482 | −0.65 | 0.64 | −1.57 | 14 |
| 1382372_at | Aryl hydrocarbon receptor | −5.07 | 0.00007 | 0.00680 | −0.74 | 0.60 | −1.67 | 14 |
| 1382430_at | similar to KIAA1585 protein (predicted) | −5.62 | 0.00002 | 0.00338 | −0.58 | 0.67 | −1.50 | 14 |

TABLE 20-continued

| Gene-ID | Gene name | t | p-value | FDR | SLR | Fold change | Affy Fold.change | df |
|---|---|---|---|---|---|---|---|---|
| 1382434_at | ectonucleoside triphosphate diphosphohydrolase 5 | −5.89 | 0.00001 | 0.00229 | −0.73 | 0.60 | −1.66 | 14 |
| 1382466_at | similar to RIKEN cDNA 6530403A03 (predicted) | −5.43 | 0.00003 | 0.00433 | −0.98 | 0.51 | −1.97 | 14 |
| 1382551_at | similar to Intersectin 2 (SH3 domain-containing protein 1B) (SH3P18) (SH3P18-like WASP associated protein) | −6.72 | 0.00000 | 0.00080 | −1.41 | 0.38 | −2.67 | 14 |
| 1382558_at | transcription factor 3 (predicted) | −6.13 | 0.00001 | 0.00171 | −0.62 | 0.65 | −1.54 | 14 |
| 1382573_at | Transcribed locus | 5.08 | 0.00007 | 0.00677 | 0.38 | 1.30 | 1.30 | 14 |
| 1382584_at | similar to mKIAA1321 protein | −7.22 | 0.00000 | 0.00042 | −1.15 | 0.45 | −2.22 | 14 |
| 1382620_at | ankyrin repeat domain 11 (predicted) | −9.69 | 0.00000 | 0.00003 | −0.95 | 0.52 | −1.93 | 14 |
| 1382797_at | similar to 1500019C06Rik protein | −5.02 | 0.00008 | 0.00742 | −0.47 | 0.72 | −1.39 | 14 |
| 1382813_at | similar to RIKEN cDNA 4930444A02 (predicted) | −5.36 | 0.00004 | 0.00467 | −0.46 | 0.73 | −1.38 | 14 |
| 1382862_at | Transcribed locus | −6.23 | 0.00001 | 0.00153 | −1.16 | 0.45 | −2.23 | 14 |
| 1382904_at | similar to hypothetical protein DKFZp434K1421 (predicted) | −9.04 | 0.00000 | 0.00005 | −0.85 | 0.56 | −1.80 | 14 |
| 1382935_at | similar to Hypothetical protein KIAA0141 | −6.54 | 0.00000 | 0.00097 | −0.64 | 0.64 | −1.56 | 14 |
| 1382939_at | translocated promoter region (predicted) | −5.18 | 0.00005 | 0.00581 | −1.13 | 0.46 | −2.19 | 14 |
| 1382957_at | similar to cisplatin resistance-associated overexpressed protein (predicted) | −8.04 | 0.00000 | 0.00016 | −1.08 | 0.47 | −2.11 | 14 |
| 1382960_at | Transcribed locus | −5.95 | 0.00001 | 0.00208 | −0.77 | 0.59 | −1.70 | 14 |
| 1382972_at | Transcribed locus, strongly similar to XP_226713.2 PREDICTED: similar to Src-associated protein SAW [Rattus norvegicus] | 5.17 | 0.00005 | 0.00595 | 0.37 | 1.29 | 1.29 | 14 |
| 1383008_at | SMC4 structural maintenance of chromosomes 4-like 1 (yeast) (predicted) | −5.19 | 0.00005 | 0.00581 | −0.98 | 0.51 | −1.97 | 14 |
| 1383040_a_at |  | −5.46 | 0.00003 | 0.00419 | −0.47 | 0.72 | −1.38 | 14 |
| 1383052_a_at |  | −6.54 | 0.00000 | 0.00097 | −0.62 | 0.65 | −1.53 | 14 |
| 1383054_at |  | −7.86 | 0.00000 | 0.00019 | −0.76 | 0.59 | −1.70 | 14 |
| 1383060_at | G kinase anchoring protein 1 (predicted) | −5.82 | 0.00001 | 0.00255 | −0.44 | 0.74 | −1.35 | 14 |
| 1383085_at | Similar to Sh3bgrl protein | −5.20 | 0.00005 | 0.00576 | −0.86 | 0.55 | −1.81 | 14 |
| 1383179_at | Similar to hypothetical protein HSPC129 (predicted) | −5.10 | 0.00006 | 0.00660 | −0.75 | 0.60 | −1.68 | 14 |
| 1383184_at | zinc and ring finger 1 (predicted) | 5.03 | 0.00007 | 0.00731 | 0.39 | 1.31 | 1.31 | 14 |
| 1383334_at | Transcribed locus | −5.37 | 0.00003 | 0.00461 | −0.46 | 0.73 | −1.37 | 14 |
| 1383455_at | glutamyl-prolyl-tRNA synthetase (predicted) | −6.80 | 0.00000 | 0.00072 | −0.72 | 0.61 | −1.65 | 14 |
| 1383535_at | ankyrin repeat and SOCS box-containing protein 8 (predicted) | 6.24 | 0.00001 | 0.00152 | 0.38 | 1.30 | 1.30 | 14 |
| 1383615_a_at | similar to HECT domain containing 1 | −6.06 | 0.00001 | 0.00178 | −1.08 | 0.47 | −2.11 | 14 |
| 1383687_at |  | −5.40 | 0.00003 | 0.00441 | −0.43 | 0.74 | −1.34 | 14 |
| 1383776_at | Transcribed locus | 6.41 | 0.00000 | 0.00120 | 0.62 | 1.54 | 1.54 | 14 |
| 1383786_at | Transcribed locus | −5.13 | 0.00006 | 0.00628 | −0.50 | 0.71 | −1.41 | 14 |
| 1383825_at | radixin | −9.20 | 0.00000 | 0.00005 | −1.01 | 0.50 | −2.01 | 14 |
| 1383827_at | tousled-like kinase 1 (predicted) | −6.09 | 0.00001 | 0.00178 | −1.25 | 0.42 | −2.37 | 14 |
| 1384125_at | myeloid/lymphoid or mixed-lineage leukemia 5 (trithorax homolog, Drosophila) (predicted) | −5.97 | 0.00001 | 0.00202 | −0.51 | 0.70 | −1.42 | 14 |
| 1384131_at | ADP-ribosylation factor-like 6 interacting protein 2 (predicted) | 6.10 | 0.00001 | 0.00176 | 0.70 | 1.63 | 1.63 | 14 |
| 1384146_at | Similar to CD69 antigen (p60, early T-cell activation antigen) | −5.22 | 0.00005 | 0.00568 | −1.35 | 0.39 | −2.55 | 14 |
| 1384154_at | WW domain binding protein 4 | −5.33 | 0.00004 | 0.00483 | −0.52 | 0.70 | −1.43 | 14 |
| 1384260_at | Transcribed locus | −6.36 | 0.00000 | 0.00126 | −0.66 | 0.63 | −1.58 | 14 |
| 1384263_at | ATP-binding cassette, sub-family A (ABC1), member 13 (predicted) similar to hypothetical protein MGC33214 (predicted) | −7.27 | 0.00000 | 0.00040 | −0.72 | 0.61 | −1.64 | 14 |

TABLE 20-continued

| Gene-ID | Gene name | t | p-value | FDR | SLR | Fold change | Affy Fold.change | df |
|---|---|---|---|---|---|---|---|---|
| 1384339_s_at | casein kinase II, alpha 1 polypeptide | −8.81 | 0.00000 | 0.00006 | −1.83 | 0.28 | −3.56 | 14 |
| 1384376_at | similar to FLJ14281 protein | −5.42 | 0.00003 | 0.00436 | −0.65 | 0.64 | −1.57 | 14 |
| 1384394_at | | −7.21 | 0.00000 | 0.00042 | −0.61 | 0.65 | −1.53 | 14 |
| 1384609_a_at | similar to RIKEN cDNA B230380D07 (predicted) | −6.61 | 0.00000 | 0.00090 | −0.91 | 0.53 | −1.87 | 14 |
| 1384766_a_at | similar to PHD finger protein 14 isoform 1 | −5.18 | 0.00005 | 0.00581 | −0.70 | 0.61 | −1.63 | 14 |
| 1384791_at | UDP-GlcNAc: betaGal beta-1,3-N-acetylglucosaminyltransferase 1 (predicted) | −5.08 | 0.00006 | 0.00671 | −0.75 | 0.60 | −1.68 | 14 |
| 1384792_at | formin binding protein 3 (predicted) | −6.70 | 0.00000 | 0.00082 | −0.97 | 0.51 | −1.96 | 14 |
| 1384857_at | A kinase (PRKA) anchor protein (yotiao) 9 | −5.62 | 0.00002 | 0.00338 | −1.05 | 0.48 | −2.07 | 14 |
| 1385006_at | alpha thalassemia/mental retardation syndrome X-linked homolog (human) | −4.94 | 0.00009 | 0.00829 | −0.45 | 0.73 | −1.37 | 14 |
| 1385038_at | similar to hedgehog-interacting protein | −9.94 | 0.00000 | 0.00003 | −0.80 | 0.57 | −1.75 | 14 |
| 1385076_at | | −5.78 | 0.00001 | 0.00271 | −0.57 | 0.68 | −1.48 | 14 |
| 1385077_at | similar to golgi-specific brefeldin A-resistance guanine nucleotide exchange factor 1 (predicted) | −7.83 | 0.00000 | 0.00019 | −1.05 | 0.48 | −2.07 | 14 |
| 1385101_a_at | Unknown (protein for MGC: 73017) | −5.53 | 0.00002 | 0.00383 | −0.97 | 0.51 | −1.96 | 14 |
| 1385108_at | Transcribed locus | −4.83 | 0.00011 | 0.00946 | −1.27 | 0.42 | −2.40 | 14 |
| 1385240_at | WD repeat domain 33 (predicted) | −4.81 | 0.00012 | 0.00958 | −0.93 | 0.52 | −1.91 | 14 |
| 1385320_at | similar to Pdz-containing protein | −5.26 | 0.00004 | 0.00530 | −0.47 | 0.72 | −1.38 | 14 |
| 1385407_at | TCDD-inducible poly(ADP-ribose) polymerase (predicted) | −5.46 | 0.00003 | 0.00417 | −1.34 | 0.39 | −2.54 | 14 |
| 1385408_at | similar to mKIAA0518 protein | −5.86 | 0.00001 | 0.00236 | −1.31 | 0.40 | −2.49 | 14 |
| 1385689_at | Transcribed locus | −4.83 | 0.00011 | 0.00948 | −0.68 | 0.62 | −1.60 | 14 |
| 1385852_at | CREB binding protein hypothetical gene supported by NM_133381 | −4.85 | 0.00011 | 0.00927 | −0.53 | 0.69 | −1.44 | 14 |
| 1385931_at | hook homolog 3 | −7.30 | 0.00000 | 0.00040 | −1.66 | 0.32 | −3.16 | 14 |
| 1385999_at | YME1-like 1 (S. cerevisiae) | −4.80 | 0.00012 | 0.00964 | −0.63 | 0.64 | −1.55 | 14 |
| 1386191_a_at | Transcribed locus | 5.22 | 0.00005 | 0.00568 | 0.46 | 1.37 | 1.37 | 14 |
| 1386641_at | Transcribed locus | −5.41 | 0.00003 | 0.00440 | −0.97 | 0.51 | −1.95 | 14 |
| 1386793_at | similar to zinc finger protein 61 | −5.28 | 0.00004 | 0.00514 | −0.59 | 0.66 | −1.51 | 14 |
| 1387087_at | CCAAT/enhancer binding protein (C/EBP), beta | −5.43 | 0.00003 | 0.00435 | −0.61 | 0.66 | −1.52 | 14 |
| 1387306_a_at | early growth response 2 | 4.82 | 0.00012 | 0.00950 | 0.33 | 1.26 | 1.26 | 14 |
| 1387365_at | nuclear receptor subfamily 1, group H, member 3 | −4.86 | 0.00011 | 0.00913 | −0.35 | 0.78 | −1.27 | 14 |
| 1387415_a_at | syntaxin binding protein 5 (tomosyn) | 4.86 | 0.00011 | 0.00913 | 0.40 | 1.32 | 1.32 | 14 |
| 1387458_at | ring finger protein 4 | 7.05 | 0.00000 | 0.00051 | 0.75 | 1.69 | 1.69 | 14 |
| 1387664_at | ATPase, H+ transporting, V1 subunit B, isoform 2 | 5.55 | 0.00002 | 0.00375 | 0.46 | 1.38 | 1.38 | 14 |
| 1387757_at | liver regeneration p-53 related protein | 5.19 | 0.00005 | 0.00581 | 0.51 | 1.42 | 1.42 | 14 |
| 1387760_a_at | one cut domain, family member 1 | −6.12 | 0.00001 | 0.00171 | −1.58 | 0.34 | −2.98 | 14 |
| 1387789_at | v-ets erythroblastosis virus E26 oncogene like (avian) | −6.61 | 0.00000 | 0.00090 | −0.58 | 0.67 | −1.50 | 14 |
| 1387915_at | Ratsg2 | −4.79 | 0.00013 | 0.00976 | −0.33 | 0.79 | −1.26 | 14 |
| 1387947_at | v-maf musculoaponeurotic fibrosarcoma oncogene family, protein B (avian) | −5.08 | 0.00007 | 0.00674 | −0.80 | 0.57 | −1.74 | 14 |
| 1388022_a_at | dynamin 1-like | 4.95 | 0.00009 | 0.00811 | 0.43 | 1.35 | 1.35 | 14 |
| 1388059_a_at | solute carrier family 11 (proton-coupled divalent metal ion transporters), member 2 | 5.75 | 0.00001 | 0.00280 | 0.43 | 1.35 | 1.35 | 14 |
| 1388089_a_at | ring finger protein 4 | 5.73 | 0.00002 | 0.00289 | 0.50 | 1.41 | 1.41 | 14 |
| 1388157_at | myristoylated alanine rich protein kinase C substrate | −5.76 | 0.00001 | 0.00276 | −0.51 | 0.70 | −1.43 | 14 |
| 1388196_at | NCK-associated protein 1 | 5.31 | 0.00004 | 0.00500 | 0.48 | 1.40 | 1.40 | 14 |
| 1388251_at | protein kinase C, lambda | 5.21 | 0.00005 | 0.00571 | 0.55 | 1.47 | 1.47 | 14 |
| 1388313_at | ribosomal protein s25 | −4.83 | 0.00011 | 0.00946 | −0.63 | 0.65 | −1.54 | 14 |

TABLE 20-continued

| Gene-ID | Gene name | t | p-value | FDR | SLR | Fold change | Affy Fold.change | df |
|---|---|---|---|---|---|---|---|---|
| 1388353_at | proliferation-associated 2G4, 38 kDa | −6.35 | 0.00000 | 0.00127 | −0.67 | 0.63 | −1.59 | 14 |
| 1388388_at | Protein phosphatase 2, regulatory subunit B (B56), delta isoform (predicted) | −5.32 | 0.00004 | 0.00487 | −0.41 | 0.75 | −1.33 | 14 |
| 1388396_at | serine/threonine kinase 25 (STE20 homolog, yeast) | −5.49 | 0.00003 | 0.00404 | −0.34 | 0.79 | −1.27 | 14 |
| 1388503_at | similar to CREBBP/EP300 inhibitory protein 1 | −6.06 | 0.00001 | 0.00178 | −0.40 | 0.76 | −1.32 | 14 |
| 1388714_at | elongation factor RNA polymerase II (predicted) | −5.88 | 0.00001 | 0.00229 | −0.46 | 0.73 | −1.37 | 14 |
| 1388735_at | Similar to keratin associated protein 10-6 | 4.84 | 0.00011 | 0.00945 | 0.50 | 1.41 | 1.41 | 14 |
| 1388752_at | BCL2-associated transcription factor 1 (predicted) | −4.81 | 0.00012 | 0.00958 | −0.40 | 0.76 | −1.32 | 14 |
| 1388849_at | Protease, serine, 25 (predicted) | −5.97 | 0.00001 | 0.00202 | −0.50 | 0.71 | −1.41 | 14 |
| 1388888_at | Transcribed locus | 5.13 | 0.00006 | 0.00632 | 0.40 | 1.32 | 1.32 | 14 |
| 1389268_at | similar to DNA polymerase lambda | −5.21 | 0.00005 | 0.00571 | −0.37 | 0.77 | −1.29 | 14 |
| 1389307_at | similar to Amyloid beta (A4) precursor-like protein 1 | −4.91 | 0.00010 | 0.00854 | −0.49 | 0.71 | −1.40 | 14 |
| 1389419_at | Transcribed locus | −6.54 | 0.00000 | 0.00097 | −1.30 | 0.40 | −2.47 | 14 |
| 1389432_at | pre-B-cell leukemia transcription factor 2 | −4.93 | 0.00009 | 0.00829 | −0.55 | 0.69 | −1.46 | 14 |
| 1389444_at | Transcribed locus | −6.84 | 0.00000 | 0.00068 | −1.06 | 0.48 | −2.09 | 14 |
| 1389806_at | Transcribed locus | −7.63 | 0.00000 | 0.00026 | −0.54 | 0.69 | −1.46 | 14 |
| 1389868_at | similar to RCK | −6.34 | 0.00000 | 0.00128 | −1.47 | 0.36 | −2.76 | 14 |
| 1389963_at | P55 mRNA for p55 protein | −5.54 | 0.00002 | 0.00378 | −0.44 | 0.74 | −1.35 | 14 |
| 1389986_at | LOC499304 | −5.39 | 0.00003 | 0.00449 | −2.57 | 0.17 | −5.93 | 14 |
| 1389989_at | alpha thalassemia/mental retardation syndrome X-linked homolog (human) | −4.93 | 0.00009 | 0.00829 | −0.54 | 0.69 | −1.45 | 14 |
| 1389998_at | Nuclear receptor subfamily 2, group F, member 2 | −6.03 | 0.00001 | 0.00187 | −0.69 | 0.62 | −1.61 | 14 |
| 1390048_at | serine/arginine repetitive matrix 2 (predicted) | −5.81 | 0.00001 | 0.00256 | −1.04 | 0.49 | −2.05 | 14 |
| 1390120_a_at | ring finger protein 1 | −5.70 | 0.00002 | 0.00299 | −0.36 | 0.78 | −1.28 | 14 |
| 1390121_at | GLIS family zinc finger 2 (predicted) | 4.81 | 0.00012 | 0.00958 | 0.43 | 1.34 | 1.34 | 14 |
| 1390227_at | CDNA clone IMAGE: 7300848 | −5.91 | 0.00001 | 0.00219 | −1.03 | 0.49 | −2.04 | 14 |
| 1390360_a_at | similar to Safb2 protein | −4.79 | 0.00013 | 0.00976 | −0.48 | 0.72 | −1.39 | 14 |
| 1390410_at | Transcribed locus | −4.79 | 0.00012 | 0.00973 | −0.49 | 0.71 | −1.40 | 14 |
| 1390436_at | Autophagy 7-like (S. cerevisiae) (predicted) | −7.88 | 0.00000 | 0.00019 | −1.46 | 0.36 | −2.76 | 14 |
| 1390448_at | similar to 1110065L07Rik protein (predicted) | 5.08 | 0.00007 | 0.00674 | 0.32 | 1.25 | 1.25 | 14 |
| 1390454_at | 4-nitrophenylphosphatase domain and non-neuronal SNAP25-like protein homolog 1 (C. elegans) (predicted) | −5.47 | 0.00003 | 0.00415 | −0.41 | 0.75 | −1.33 | 14 |
| 1390576_at | Transcribed locus | −5.10 | 0.00006 | 0.00660 | −0.67 | 0.63 | −1.59 | 14 |
| 1390660_at | T-box 2 (predicted) | 5.01 | 0.00008 | 0.00752 | 0.40 | 1.32 | 1.32 | 14 |
| 1390706_at | spectrin beta 2 | −5.55 | 0.00002 | 0.00376 | −0.71 | 0.61 | −1.64 | 14 |
| 1390739_at | similar to zinc finger protein 609 similar to zinc finger protein 609 | −5.51 | 0.00003 | 0.00395 | −0.52 | 0.70 | −1.43 | 14 |
| 1390777_at | sterol-C5-desaturase (fungal ERG3, delta-5-desaturase) homolog (S. cerevisae) | −6.59 | 0.00000 | 0.00090 | −0.70 | 0.61 | −1.63 | 14 |
| 1390779_at | Similar to phosphoseryl-tRNA kinase | −4.86 | 0.00011 | 0.00913 | −0.64 | 0.64 | −1.56 | 14 |
| 1390813_at | Similar to RNA-binding protein Musashi2-S | −5.19 | 0.00005 | 0.00581 | −0.62 | 0.65 | −1.54 | 14 |
| 1390884_a_at | UDP-GlcNAc: betaGal beta-1,3-N-acetylglucosaminyltransferase 7 (predicted) | 4.87 | 0.00010 | 0.00904 | 0.49 | 1.40 | 1.40 | 14 |
| 1391021_at | similar to KIAA1749 protein (predicted) | −7.55 | 0.00000 | 0.00027 | −0.74 | 0.60 | −1.67 | 14 |
| 1391170_at | similar to mKIAA1757 protein (predicted) | −9.21 | 0.00000 | 0.00005 | −2.01 | 0.25 | −4.04 | 14 |
| 1391222_at | similar to Nedd4 binding protein 1 (predicted) | −5.91 | 0.00001 | 0.00219 | −0.81 | 0.57 | −1.76 | 14 |
| 1391297_at | REST corepressor 1 (predicted) | −5.17 | 0.00005 | 0.00595 | −0.92 | 0.53 | −1.89 | 14 |

TABLE 20-continued

| Gene-ID | Gene name | t | p-value | FDR | SLR | Fold change | Affy Fold.change | df |
|---|---|---|---|---|---|---|---|---|
| 1391578_at | | −8.48 | 0.00000 | 0.00009 | −1.11 | 0.46 | −2.15 | 14 |
| 1391584_at | Transcribed locus | 6.04 | 0.00001 | 0.00185 | 0.45 | 1.37 | 1.37 | 14 |
| 1391625_at | Wiskott-Aldrich syndrome-like (human) | −10.52 | 0.00000 | 0.00002 | −1.28 | 0.41 | −2.43 | 14 |
| 1391669_at | protein tyrosine phosphatase, receptor type, B (predicted) | −6.21 | 0.00001 | 0.00156 | −0.82 | 0.56 | −1.77 | 14 |
| 1391689_at | similar to Retinoblastoma-binding protein 2 (RBBP-2) | −9.06 | 0.00000 | 0.00005 | −1.20 | 0.44 | −2.30 | 14 |
| 1391701_at | MYST histone acetyltransferase (monocytic leukemia) 3 (predicted) | −5.18 | 0.00005 | 0.00581 | −0.98 | 0.51 | −1.97 | 14 |
| 1391743_at | ELAV (embryonic lethal, abnormal vision, Drosophila)-like 1 (Hu antigen R) (predicted) | −4.80 | 0.00012 | 0.00964 | −1.36 | 0.39 | −2.58 | 14 |
| 1391830_at | copine VIII (predicted) | −5.22 | 0.00005 | 0.00568 | −1.08 | 0.47 | −2.12 | 14 |
| 1391838_at | ankyrin repeat domain 11 (predicted) | −7.81 | 0.00000 | 0.00019 | −1.15 | 0.45 | −2.23 | 14 |
| 1391848_at | RNA binding motif protein 27 (predicted) | −7.02 | 0.00000 | 0.00053 | −0.76 | 0.59 | −1.70 | 14 |
| 1391968_at | Similar to expressed sequence AA415817 | −4.89 | 0.00010 | 0.00883 | −0.69 | 0.62 | −1.62 | 14 |
| 1392000_at | Similar to PHD finger protein 14 isoform 1 | 5.01 | 0.00008 | 0.00742 | 0.45 | 1.37 | 1.37 | 14 |
| 1392061_at | minichromosome maintenance deficient 10 (S. cerevisiae) (predicted) | 5.34 | 0.00004 | 0.00482 | 0.54 | 1.46 | 1.46 | 14 |
| 1392269_at | transcriptional regulator, SIN3A (yeast) (predicted) | −6.23 | 0.00001 | 0.00153 | −1.13 | 0.46 | −2.19 | 14 |
| 1392277_at | | −7.29 | 0.00000 | 0.00040 | −0.48 | 0.72 | −1.40 | 14 |
| 1392322_at | GTPase, IMAP family member 7 | −4.83 | 0.00012 | 0.00948 | −0.29 | 0.82 | −1.22 | 14 |
| 1392472_at | similar to myocyte enhancer factor 2C | −9.77 | 0.00000 | 0.00003 | −0.88 | 0.54 | −1.84 | 14 |
| 1392552_at | similar to transcription repressor p66 (predicted) | −6.15 | 0.00001 | 0.00169 | −0.96 | 0.51 | −1.95 | 14 |
| 1392564_at | myeloid/lymphoid or mixed-lineage leukemia 5 (trithorax homolog, Drosophila) (predicted) | −6.13 | 0.00001 | 0.00171 | −0.57 | 0.68 | −1.48 | 14 |
| 1392629_a_at | similar to MADP-1 protein (predicted) | −4.93 | 0.00009 | 0.00829 | −0.82 | 0.57 | −1.77 | 14 |
| 1392738_at | similar to KIAA1096 protein | −5.88 | 0.00001 | 0.00231 | −0.75 | 0.59 | −1.68 | 14 |
| 1392825_at | LOC499256 | −5.20 | 0.00005 | 0.00580 | −0.93 | 0.53 | −1.90 | 14 |
| 1392864_at | Rho GTPase activating protein 5 (predicted) | −8.05 | 0.00000 | 0.00016 | −1.37 | 0.39 | −2.58 | 14 |
| 1392932_at | leukocyte receptor cluster (LRC) member 8 (predicted) | −4.81 | 0.00012 | 0.00958 | −0.79 | 0.58 | −1.73 | 14 |
| 1392936_at | similar to RNA binding motif protein 25 | −4.82 | 0.00012 | 0.00950 | −0.88 | 0.54 | −1.85 | 14 |
| 1392984_at | copine III (predicted) | −7.83 | 0.00000 | 0.00019 | −0.95 | 0.52 | −1.93 | 14 |
| 1393151_at | | 5.03 | 0.00007 | 0.00726 | 0.65 | 1.57 | 1.57 | 14 |
| 1393226_at | Transcribed locus | −4.94 | 0.00009 | 0.00828 | −0.73 | 0.60 | −1.66 | 14 |
| 1393290_at | similar to myocyte enhancer factor 2C | −5.65 | 0.00002 | 0.00327 | −0.50 | 0.71 | −1.42 | 14 |
| 1393322_at | TAF15 RNA polymerase II, TATA box binding protein (TBP)-associated factor (predicted) | −6.18 | 0.00001 | 0.00162 | −1.00 | 0.50 | −2.00 | 14 |
| 1393378_at | | −5.72 | 0.00002 | 0.00293 | −0.52 | 0.70 | −1.43 | 14 |
| 1393443_a_at | similar to CGI-112 protein (predicted) | −5.33 | 0.00004 | 0.00483 | −0.47 | 0.72 | −1.39 | 14 |
| 1393505_x_at | similar to RIKEN cDNA B230380D07 (predicted) | −7.60 | 0.00000 | 0.00026 | −0.69 | 0.62 | −1.61 | 14 |
| 1393511_at | similar to galactose-3-O-sulfotransferase 4 | 5.10 | 0.00006 | 0.00655 | 0.41 | 1.33 | 1.33 | 14 |
| 1393560_at | | −4.91 | 0.00010 | 0.00852 | −0.51 | 0.70 | −1.42 | 14 |
| 1393576_at | Transcribed locus | −4.82 | 0.00012 | 0.00950 | −0.62 | 0.65 | −1.54 | 14 |
| 1393593_at | similar to KIAA0597 protein | 5.43 | 0.00003 | 0.00435 | 0.57 | 1.48 | 1.48 | 14 |
| 1393639_at | myosin X (predicted) | −4.95 | 0.00009 | 0.00811 | −0.59 | 0.67 | −1.50 | 14 |
| 1393790_at | HRAS-like suppressor (predicted) | 5.44 | 0.00003 | 0.00432 | 0.44 | 1.35 | 1.35 | 14 |
| 1393798_at | alpha thalassemia/mental retardation syndrome X-linked homolog (human) | −5.00 | 0.00008 | 0.00757 | −0.84 | 0.56 | −1.79 | 14 |
| 1393804_at | similar to hypothetical protein FLJ22490 (predicted) | −6.79 | 0.00000 | 0.00073 | −0.85 | 0.56 | −1.80 | 14 |

TABLE 20-continued

| Gene-ID | Gene name | t | p-value | FDR | SLR | Fold change | Affy Fold.change | df |
|---|---|---|---|---|---|---|---|---|
| 1393809_at | Tnf receptor-associated factor 6 (predicted) | −8.48 | 0.00000 | 0.00009 | −0.90 | 0.53 | −1.87 | 14 |
| 1393811_at | similar to putative repair and recombination helicase RAD26L | −6.08 | 0.00001 | 0.00178 | −0.79 | 0.58 | −1.73 | 14 |
| 1393910_at | similar to Fam13a1 protein (predicted) | −4.85 | 0.00011 | 0.00921 | −0.81 | 0.57 | −1.75 | 14 |
| 1393981_at | similar to KIAA0423 (predicted) | −5.24 | 0.00005 | 0.00556 | −0.57 | 0.68 | −1.48 | 14 |
| 1394003_at | similar to DNA polymerase epsilon p17 subunit (DNA polymerase epsilon subunit 3) (Chromatin accessibility complex 17) (HuCHRAC17) (CHRAC-17) | −5.59 | 0.00002 | 0.00349 | −0.59 | 0.67 | −1.50 | 14 |
| 1394220_at | Similar to hypothetical protein (predicted) | 5.46 | 0.00003 | 0.00417 | 0.43 | 1.34 | 1.34 | 14 |
| 1394243_at | similar to spermine synthase | −6.11 | 0.00001 | 0.00175 | −0.60 | 0.66 | −1.51 | 14 |
| 1394436_at | sperm associated antigen 9 (predicted) | −6.60 | 0.00000 | 0.00090 | −0.91 | 0.53 | −1.88 | 14 |
| 1394497_at | similar to TCF7L2 protein | −8.03 | 0.00000 | 0.00016 | −1.06 | 0.48 | −2.08 | 14 |
| 1394594_at | Transcribed locus | 5.09 | 0.00006 | 0.00671 | 0.42 | 1.34 | 1.34 | 14 |
| 1394715_at | Dicer1, Dcr-1 homolog (*Drosophila*) (predicted) | 5.14 | 0.00006 | 0.00627 | 0.54 | 1.46 | 1.46 | 14 |
| 1394740_at | | 5.41 | 0.00003 | 0.00440 | 0.52 | 1.43 | 1.43 | 14 |
| 1394742_at | Transcribed locus | −5.73 | 0.00002 | 0.00289 | −0.98 | 0.51 | −1.98 | 14 |
| 1394746_at | hect (homologous to the E6-AP (UBE3A) carboxyl terminus) domain and RCC1 (CHC1)-like domain (RLD) 1 (predicted) | −7.32 | 0.00000 | 0.00039 | −0.94 | 0.52 | −1.91 | 14 |
| 1394814_at | translocated promoter region (predicted) | −6.13 | 0.00001 | 0.00171 | −0.63 | 0.64 | −1.55 | 14 |
| 1394849_at | Transcribed locus | −5.22 | 0.00005 | 0.00569 | −1.61 | 0.33 | −3.05 | 14 |
| 1394865_at | Transmembrane protein 7 (predicted) | −7.85 | 0.00000 | 0.00019 | −0.92 | 0.53 | −1.90 | 14 |
| 1394965_at | enthoprotin | 5.30 | 0.00004 | 0.00503 | 0.40 | 1.32 | 1.32 | 14 |
| 1394969_at | Transcribed locus | 5.40 | 0.00003 | 0.00441 | 0.39 | 1.31 | 1.31 | 14 |
| 1394985_at | early endosome antigen 1 (predicted) | −7.60 | 0.00000 | 0.00026 | −1.00 | 0.50 | −2.00 | 14 |
| 1395211_s_at | supervillin (predicted) | −8.74 | 0.00000 | 0.00007 | −0.98 | 0.51 | −1.97 | 14 |
| 1395237_at | eukaryotic translation initiation factor 5B | −8.31 | 0.00000 | 0.00012 | −0.87 | 0.55 | −1.83 | 14 |
| 1395264_at | similar to Rap1-interacting factor 1 | −6.85 | 0.00000 | 0.00067 | −0.95 | 0.52 | −1.93 | 14 |
| 1395331_at | similar to hypothetical protein CL25084 (predicted) | 4.84 | 0.00011 | 0.00945 | 0.31 | 1.24 | 1.24 | 14 |
| 1395338_at | leucine-rich PPR-motif containing (predicted) | 5.24 | 0.00005 | 0.00555 | 0.75 | 1.68 | 1.68 | 14 |
| 1395516_at | similar to hypothetical protein FLJ10154 (predicted) | −4.89 | 0.00010 | 0.00883 | −0.59 | 0.66 | −1.51 | 14 |
| 1395565_at | COP9 signalosome subunit 4 | 5.55 | 0.00002 | 0.00376 | 0.40 | 1.32 | 1.32 | 14 |
| 1395610_at | similar to Hypothetical protein MGC30714 | 5.66 | 0.00002 | 0.00325 | 0.33 | 1.26 | 1.26 | 14 |
| 1395616_at | similar to Ab2-008 (predicted) | −5.03 | 0.00007 | 0.00729 | −0.50 | 0.71 | −1.42 | 14 |
| 1395625_at | Transcribed locus | −6.03 | 0.00001 | 0.00187 | −0.76 | 0.59 | −1.70 | 14 |
| 1395739_at | similar to RIKEN cDNA C920006C10 (predicted) | 5.05 | 0.00007 | 0.00698 | 0.54 | 1.46 | 1.46 | 14 |
| 1395814_at | Transcribed locus | −5.09 | 0.00006 | 0.00663 | −0.78 | 0.58 | −1.71 | 14 |
| 1395976_at | similar to phosphoinositol 4-phosphate adaptor protein-2 | −6.37 | 0.00000 | 0.00126 | −0.57 | 0.67 | −1.49 | 14 |
| 1395981_at | helicase, ATP binding 1 (predicted) | −5.76 | 0.00001 | 0.00276 | −0.62 | 0.65 | −1.54 | 14 |
| 1396036_at | Ral GEF with PH domain and SH3 binding motif 2 (predicted) | −6.67 | 0.00000 | 0.00084 | −1.04 | 0.49 | −2.06 | 14 |
| 1396063_at | DEK oncogene (DNA binding) | −4.82 | 0.00012 | 0.00952 | −0.63 | 0.65 | −1.55 | 14 |
| 1396100_at | similar to RIKEN cDNA 2010009L17 (predicted) | −5.15 | 0.00006 | 0.00610 | −0.56 | 0.68 | −1.47 | 14 |
| 1396170_at | WW domain binding protein 4 | −7.78 | 0.00000 | 0.00020 | −0.77 | 0.59 | −1.71 | 14 |
| 1396187_at | Hypothetical protein LOC606294 | 5.14 | 0.00006 | 0.00622 | 0.51 | 1.43 | 1.43 | 14 |
| 1396202_at | Transcribed locus | 4.97 | 0.00008 | 0.00795 | 0.52 | 1.44 | 1.44 | 14 |
| 1396403_at | | −9.07 | 0.00000 | 0.00005 | −1.01 | 0.50 | −2.02 | 14 |
| 1396803_at | similar to THO complex 2 | −7.09 | 0.00000 | 0.00050 | −0.90 | 0.54 | −1.86 | 14 |

TABLE 20-continued

| Gene-ID | Gene name | t | p-value | FDR | SLR | Fold change | Affy Fold.change | df |
|---|---|---|---|---|---|---|---|---|
| 1397203_at | PRP4 pre-mRNA processing factor 4 homolog B (yeast) (predicted) | −6.18 | 0.00001 | 0.00162 | −0.67 | 0.63 | −1.59 | 14 |
| 1397234_at | G patch domain containing 1 (predicted) | −5.65 | 0.00002 | 0.00326 | −0.49 | 0.71 | −1.40 | 14 |
| 1397367_at | A disintegrin and metalloprotease domain 23 (predicted) | 5.05 | 0.00007 | 0.00698 | 0.47 | 1.38 | 1.38 | 14 |
| 1397508_at | similar to RIKEN cDNA 2310005B10 | −5.08 | 0.00006 | 0.00671 | −0.62 | 0.65 | −1.54 | 14 |
| 1397552_at | echinoderm microtubule associated protein like 4 (predicted) | −8.47 | 0.00000 | 0.00009 | −1.39 | 0.38 | −2.62 | 14 |
| 1397627_at | diaphanous homolog 1 (Drosophila) (predicted) | −5.07 | 0.00007 | 0.00680 | −0.52 | 0.70 | −1.43 | 14 |
| 1397647_at | solute carrier family 25 (mitochondrial carrier; ornithine transporter) member 15 (predicted) | 5.51 | 0.00003 | 0.00395 | 0.62 | 1.54 | 1.54 | 14 |
| 1397669_at | Chemokine (C-C motif) receptor 6 (predicted) | 5.78 | 0.00001 | 0.00271 | 0.51 | 1.43 | 1.43 | 14 |
| 1397674_at | eukaryotic translation initiation factor 3, subunit 8, 110 kDa (predicted) | −6.44 | 0.00000 | 0.00116 | −0.76 | 0.59 | −1.69 | 14 |
| 1397676_at | Similar to osteoclast inhibitory lectin | −6.68 | 0.00000 | 0.00084 | −1.34 | 0.39 | −2.54 | 14 |
| 1397758_at | Similar to choline phosphotransferase 1; cholinephosphotransferase 1 alpha; cholinephosphotransferase 1 | −4.83 | 0.00011 | 0.00946 | −0.38 | 0.77 | −1.30 | 14 |
| 1397959_at | similar to RIKEN cDNA D130059P03 gene (predicted) | −6.39 | 0.00000 | 0.00123 | −1.14 | 0.45 | −2.20 | 14 |
| 1398311_a_at | kinase D-interacting substance 220 | 5.14 | 0.00006 | 0.00627 | 0.44 | 1.36 | 1.36 | 14 |
| 1398351_at | Ubiquitin specific protease 7 (herpes virus-associated) (predicted) | −5.60 | 0.00002 | 0.00349 | −0.42 | 0.75 | −1.34 | 14 |
| 1398420_at | Similar to E3 ubiquitin ligase SMURF2 (predicted) | −5.33 | 0.00004 | 0.00483 | −0.94 | 0.52 | −1.92 | 14 |
| 1398436_at | ubiquitin specific protease 42 (predicted) | −6.36 | 0.00000 | 0.00126 | −0.76 | 0.59 | −1.69 | 14 |
| 1398486_at | CDNA clone MGC: 93990 IMAGE: 7115381 | −8.09 | 0.00000 | 0.00016 | −1.53 | 0.35 | −2.89 | 14 |
| 1398522_at | similar to Ab2-034 (predicted) | −4.92 | 0.00009 | 0.00832 | −0.51 | 0.70 | −1.42 | 14 |
| 1398553_at | similar to CGI-100-like protein | −6.91 | 0.00000 | 0.00062 | −1.68 | 0.31 | −3.20 | 14 |
| 1398834_at | mitogen activated protein kinase kinase 2 | −4.94 | 0.00009 | 0.00828 | −0.32 | 0.80 | −1.25 | 14 |
| 1398926_at | prefoldin 1 (predicted) | −5.95 | 0.00001 | 0.00208 | −0.48 | 0.72 | −1.40 | 14 |
| 1398963_at | TAF10 RNA polymerase II, TATA box binding protein (TBP)-associated factor (predicted) | −5.42 | 0.00003 | 0.00436 | −0.41 | 0.75 | −1.33 | 14 |
| 1399099_at | heterogeneous nuclear ribonucleoprotein U-like 1 (predicted) | −4.94 | 0.00009 | 0.00829 | −0.54 | 0.69 | −1.46 | 14 |
| 1399140_at | Transcribed locus | −5.16 | 0.00005 | 0.00597 | −0.49 | 0.71 | −1.40 | 14 |
| AFFX-BioB-M_at | Biotin synthase biotin synthesis, sulfur insertion? | −4.89 | 0.00010 | 0.00879 | −0.64 | 0.64 | −1.56 | 14 |
| AFFX-BioDn-5_at | dethiobiotin synthetase | −4.92 | 0.00009 | 0.00834 | −0.70 | 0.62 | −1.62 | 14 |
| AFFX-r2-Ec-bioD-5_at | dethiobiotin synthetase | −5.41 | 0.00003 | 0.00440 | −0.51 | 0.70 | −1.43 | 14 |

List of genes differentially expressed (DE) by MPL2 versus control. SLR: Estimated signal log-ratio (<0: down regulated gene, >0: up regulated gene). Fold change: Estimated fold change corresponding to the parameter (<1: down regulated gene, >1: up regulated gene). Affy fold change: Estimated fold change using the Affymetrix definition (<−1: down regulated gene, >1: up regulated gene) df: Degrees of freedom (=number of arrays − number of estimated parameters)

Example 7

60 g fatty acid ethyl ester consisting of 10% EPA and 50% DHA (FAEE 10-50), obtained from Napro Pharma (Brattvaag, Norway) and 15 g TL-IM obtained from Novozymes (Bagsvaerd, Denmark) were mixed in an evacuated round bottomed glass flask for 15 minutes. Next, $N_2$ was released into the glass flask and the mixture was heated to 65° C. 20 g Alcolec 40P® from American Lecithin Company Inc (Oxford, Conn., USA) was then added to the reaction mixture. Alcolec 40P® is a crude soybean phospholipid product containing 40% PC, 26% phosphatidylethanolamine, 11% phosphatidylinositol, 1% phosphatidylserine, 13% phytoglycolipids as well as 14% other phosphatides (w,w). Next, the glass flask was evacuated (20-30 mbar). Finally, a second vessel containing water (30° C.), was connected to the reaction vessel through a plastic tube (FIG. 1). The reduced pressure allowed moisture from the headspace of the second vessel to be added through the reaction mixture continuously. In order to obtain the final product the enzymes were removed by filtration. Finally, a triglyceride carrier was added to the product, followed by removal of the residual free fatty acids and/or esters by short path distillation. In order to analyze the product, the sample was fractionated by HPLC-UV ($\lambda$=207 nm) with a silica column and methanol-water (92:8, v/v) as mobile phase. The isolated PC+LPC fraction was then dried under nitrogen prior to derivatization; finally the fatty acid profile was determined by analyzing the derivatives using GC-FID. Furthermore, the relationship between PC, LPC and GPC was determined using HPLC with the method above, except that the UV detector was replaced by an evaporative light scattering detection (ELSD). Integrated ELSD peak areas were reported for PC/LPC/GPC (total 100%); however for simplicity other PL species were not analyzed. The results obtained for example 7 is shown in table 20 below.

TABLE 20

Results obtained after transesterification using vacuum and water addition

| Reaction time | PC/LPC/GPC* | EPA/DHA** | Acid value |
|---|---|---|---|
| 1 day | 65/31/4 | 3.6/2.6 | 43 |
| 2 days | 52/45/3 | 5.3/4.7 | 55 |
| 5 days | 78/22/0 | 5.2/4.6 | 65 |
| 6 days | 72/26/2 | 6.0/5.3 | 75 |

*ELSD peak area (total 100%). Only peaks relating to PC, LPC and GPC are integrated.
**EPA/DHA attached to PC + LPC Example 8

The enzymes from example 7 were isolated by filtration and the possibility of reuse was determined in the following experiment. 30 g FAEE (10-50), 10 g Alcolec and 15 g used enzymes (equivalent to 7.5 g enzyme because the used enzymes had absorbed product from the first reaction). The reaction was performed at 65° C. and stirred at 200 rpm using a shaker incubator. The transesterified phospholipids were analyzed as in the previous example and the results are shown in table 21 below.

TABLE 21

Results obtained with reused enzymes using incubator shaker

| Reaction time | PC/LPC/GPC* | EPA/DHA** | Acid value |
|---|---|---|---|
| 1 day | 94/5/1 | 0.4/0.5 | 55 |
| 2 days | 87/11/2 | 0.7/0.7 | 76 |
| 5 days | 68/26/6 | 1.0/0.8 | 85 |

*ELSD peak area (total 100%). Only peaks relating to PC, LPC and GPC are integrated.
**EPA/DHA attached to PC + LPC Example 9

The same conditions as in example 1 were used, except that the amount of lipase was 10 g. The results are shown in table 22.

TABLE 22

Results obtained with reduced lipase dosage after transesterification using vacuum and water addition

| Reaction time | PC/LPC/GPC* | EPA/DHA** | Acid value |
|---|---|---|---|
| 1 day | 90/10/0 | 0.9/0.7 | 29 |
| 2 days | 74/24/2 | 2.1/1.5 | 87 |
| 3 days | 49/27/24 | 4.6/4.4 | 102 |
| 6 days | 25/32/43 | 6.7/6.9 | 115 |

*ELSD peak area (total 100%). Only peaks relating to PC, LPC and GPC are integrated.
**EPA/DHA attached to PC + LPC Example 10

The enzymes from example 7 were isolated by filtration and the possibility of reuse was determined in the following experiment. 30 g FAEE (10-50), 10 g Alcolec and 15 g used enzymes (equivalent to 7.5 g enzyme because the used enzymes had absorbed product from the first reaction). The reaction was performed using the same conditions as in example 3. See table 23 below for results.

TABLE 23

Reuse of enzymes from example 7 using vapor addition into evacuated reaction vessel.

| Reaction time | PC/LPC/GPC* | EPA/DHA** | Acid value |
|---|---|---|---|
| 1 day | 79/17/4 | 1.0/0.9 | 55 |
| 2 days | 59/31/10 | 2.8/2.6 | 76 |
| 3 days | 52/34/14 | 3.8/3.5 | 85 |
| 6 days | 37/43/20 | 5.6/5.7 | 95 |

*ELSD peak area (total 100%). Only peaks relating to PC, LPC and GPC are integrated.
**EPA/DHA attached the fraction consisting of PC + LPC Example 11

The same conditions as in example 7 are applied, except that the pressure in the reaction vessel is 1 mbar. The results obtained are similar to the results in Table 23, except that the hydrolysis and the acid values are reduced. After 6 days the relationship between PC species is 80/10/0 and the acids value is 40. The incorporation of EPA/DHA is the same.

Example 12

The safety of omega-3 rich phospholipids prepared in the presence of chloroform and omega-7 rich phospholipids prepared under solvent free conditions is to be examined by feeding pregnant rats for 1 week. It is to be found that the treatment containing omega-3 rich phospholipids with traces of chloroform will result in damage to the developing fetus than the treatment containing essentially no traces of organic solvents.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclo-

REFERENCES

[1] WO 2006054183
[2] P. C. Calder. Prostaglandins, Leukotrienes and Essential Fatty Acids 2006; 75; 197-202.
[3] U.S. Pat. No. 5,434,183
[4] Alexander J W. *Nutrition* 14 (1998) 627.
[5] Belluzi A, Boschi S, Brignola C, Munarini A, Cariani G and Miglio F. *Am J Clin Nutr* 71 (2000) 339.
[6] Kremer J M. *Am J Clin Nutr* 71 (2000) 249
[7] V P Carnielli, G. Verlato, F. Pederzini, I. Luijendijk, A. Boerlage, D. Pedrotti and P. Sauer Am J Clin Nutr 1998; 67; 97-103.
[8] M. Moya, E. Cortes, M. Juste, J. G. De Dios and A Vera Eur. J. Clin. Nutr. 2001; 55; 755-762.
[9] A. Sala-Vila, A. I. Castello, C. Campoy, M. Rivero, M. Rodriguez-Palermoe and M. C. Lopez-Sabater. J. Nutr. 2004; 134; 868-873.
[10] A. Sala-Vila, C. Campoy, A. I. Castellote, F. J. Garrido, M. Rivero, M. Rodriguez-Palmero and M. C. Lopez-Sabater. Prostaglandins, Leukotrienes and Essential Fatty Acids; 2006; 74; 143-148.
[11] A. Valenzuela, S. Nieto, J. Sanhueza, M. J. Nunez and C. Ferrer. Annals of Nutrition & Metabolism; 2005; 49; 325-332.
[12] J. B. Hansen, S: Grimsgaard, H. Nilsen, A. Nordoy and K. H. Bonaa. Lipids; 1998; 33; 131-138.
[13] US provisional application entitled "Functional Phospholipid Compositions" with Ser. No. 60/798,027 filed May 5, 2006.
[14] P. C Calder, Philip C. Am. J. Clin. Nutr; 2006; 83; 1505S-1519S.
[15] G. G. Haraldsson, A. Thorarensen, JAOCS 76 (1999) 1143-1149.
[16] G. Lepage and C. C. Roy; J. Lipid Res; 1986; 27; 114-120.
[17] T. Moriguchi, S-Y Lim, R. Greiner, W. Lefkowitz, J. Loewke, J. Hoshiba and N. Salem. J. Lipid Res; 2004; 45; 1437-1445.
[18] H. Salman, M. Bergman, H Bessler, S Alexandrova, B. Beilin, M. Djaldetti. Acta Phys Scand; 2000; 168, 431-436.
[19] Haraldsson G G and Thorarensen A, *JAOCS* 76 (1999) 1143.
[20] Sarney D B, Fregapane G and Vulfson E N. *JAOCS* 71 (1994) 93.

The invention claimed is:

1. A gel capsule containing a lipid composition comprising a mixture of phospholipid molecules, having the following general structure:

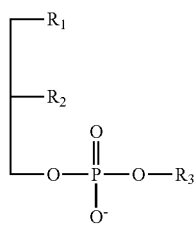

wherein R1 and R2 are a fatty acid residue or —OH and R1 and R2 are not simultaneously —OH and R3 is a choline, ethanolamine, serine or inositol group and said mixture of phospholipid molecules is characterized in comprising at least 1% docosahexaenoic acid (DHA) residues or eicosapentaenoic acid (EPA) residues at positions R1 or R2, said lipid composition has a lysophospholipid content of from 15% to 60% w/w of said composition, and said composition comprises triglycerides.

2. The gel capsule of claim 1, wherein said lipid composition has a lysophospholipid content of from 15% to 30% w/w of said composition.

3. The gel capsule of claim 1 wherein said mixture of phospholipids has a ratio of EPA/DHA residues ranging from 1:1 to 4:1.

4. The gel capsule of claim 1, wherein said mixture of phospholipids having a ratio of EPA/DHA residues ranging from 2:1 to 4:1.

5. The gel capsule of claim 1, wherein said mixture of phospholipid molecules is characterized in comprising at least 15% docosahexaenoic acid (DHA) residues or eicosapentaenoic acid (EPA) residues at positions R1 or R2.

6. The gel capsule of claim 1, wherein said mixture of phospholipid molecules is characterized in comprising at least 20% docosahexaenoic acid (DHA) residues or eicosapentaenoic acid (EPA) residues at positions R1 or R2.

7. A gel capsule containing a lipid composition comprising a mixture of phospholipid molecules, having the following general structure:

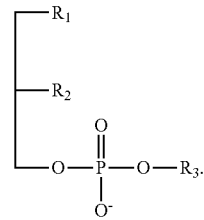

wherein R1 and R2 are a fatty acid residue or —OH and R1 and R2 are not simultaneously —OH and R3 is a choline, ethanolamine, serine or inositol group and said mixture of phospholipid molecules is characterized in comprising at least 15% docosahexaenoic acid (DHA) residues or eicosapentaenoic acid (EPA) residues at positions R1 or R2, said lipid composition has a lysophospholipid content of from 15% to 60% w/w of said composition, and said composition comprises triglycerides.

8. The gel capsule of claim 7, wherein said lipid composition has a lysophospholipid content of from 15% to 30% w/w of said composition.

9. The gel capsule of claim 7, wherein said mixture of phospholipid molecules has a ratio of EPA/DHA residues ranging from 1:1 to 4:1.

10. The gel capsule of claim 7, wherein said mixture of phospholipids having a ratio of EPA/DHA residues ranging from 2:1 to 4:1.

11. A gel capsule containing a lipid composition comprising a mixture of phospholipid molecules, having the following general structure:

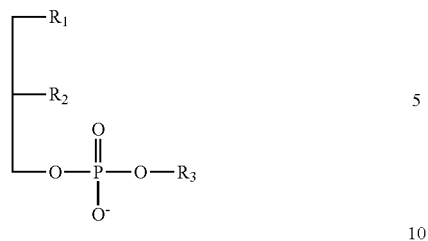

wherein R1 and R2 are a fatty acid residue or —OH and R1 and R2 are not simultaneously —OH and R3 is a choline, ethanolamine, serine or inositol group and said mixture of phospholipid molecules is characterized in comprising at least 15% docosahexaenoic acid (DHA) residues or eicosapentaenoic acid (EPA) residues at positions R1 or R2 and said lipid composition has a lysophospholipid content of from 15% to 30% w/w of said composition.

12. The gel capsule of claim 11, wherein said mixture of phospholipids has a ratio of EPA/DHA residues ranging from 1:1 to 4:1.

13. The gel capsule of claim 11, wherein said mixture of phospholipids having a ratio of EPA/DHA ranging from 2:1 to 4:1.

14. The gel capsule of claim 11, wherein said lipid composition further comprises triglycerides.

* * * * *